United States Patent
Ishii et al.

(10) Patent No.: US 9,743,958 B2
(45) Date of Patent: Aug. 29, 2017

(54) SPINAL IMPLANT AND DEVICE FOR SPINAL FIXING

(71) Applicants: KYOCERA Medical Corporation, Osaka-shi, Osaka (JP); Ken Ishii, Tokyo (JP); Morio Matsumoto, Tokyo (JP); Yoshiaki Toyama, Tokyo (JP)

(72) Inventors: Ken Ishii, Tokyo (JP); Morio Matsumoto, Tokyo (JP); Yoshiaki Toyama, Tokyo (JP); Junji Ito, Osaka (JP); Masaki Atarashi, Osaka (JP)

(73) Assignee: Kyocera Corporation, Kyoto (JP)

( * ) Notice: Subject to any disclaimer, the term of this patent is extended or adjusted under 35 U.S.C. 154(b) by 0 days.

(21) Appl. No.: 14/892,745

(22) PCT Filed: Jun. 3, 2014

(86) PCT No.: PCT/JP2014/064745
§ 371 (c)(1),
(2) Date: Nov. 20, 2015

(87) PCT Pub. No.: WO2014/196531
PCT Pub. Date: Dec. 11, 2014

(65) Prior Publication Data
US 2016/0113685 A1    Apr. 28, 2016

(30) Foreign Application Priority Data

Jun. 7, 2013 (JP) ................................ 2013-120425
May 28, 2014 (JP) ................................ 2014-110280

(51) Int. Cl.
*A61B 17/70* (2006.01)
*A61B 90/00* (2016.01)
*A61B 17/88* (2006.01)

(52) U.S. Cl.
CPC ........ *A61B 17/7032* (2013.01); *A61B 17/708* (2013.01); *A61B 17/7037* (2013.01);
(Continued)

(58) Field of Classification Search
CPC ....................... A61B 17/7032; A61B 17/7037
See application file for complete search history.

(56) References Cited

U.S. PATENT DOCUMENTS 6,648,888 B1 * 11/2003 Shluzas .............. A61B 17/7091
606/86 A
8,388,659 B1 * 3/2013 Lab .................... A61B 17/7037
606/265

(Continued)

FOREIGN PATENT DOCUMENTS

JP    2007-525274 A    9/2007
JP    2009-540879 A    11/2009

(Continued)

OTHER PUBLICATIONS

International Search Report, PCT/JP2014/064745, Jul. 15, 2014, 2 pgs.

(Continued)

*Primary Examiner* — Ellen C Hammond
*Assistant Examiner* — Stuart S Bray
(74) *Attorney, Agent, or Firm* — Volpe and Koenig, P.C.

(57) ABSTRACT

An extender is removed from a spinal implant without using a separate device, and the loss of materials to be discarded is reduced. A head part of a spinal implant includes a base part, which is provided as a portion on a screw part side, and a pair of tab parts, which extend from the base part to an opposite side to the screw part side. The pair of tab parts have a tab part-side engagement part to be engaged by an extender-side engagement part that is formed on the extender. A weak part is formed between the base part and (Continued)

the pair of tab parts, the weak part being configured to be broken by an external force from the extender engaged with the pair of tab parts and separate the pair of tab parts from the base part.

11 Claims, 19 Drawing Sheets

(52) U.S. Cl.
CPC .......... *A61B 17/8863* (2013.01); *A61B 90/03* (2016.02); *A61B 2090/037* (2016.02)

(56) References Cited

U.S. PATENT DOCUMENTS

| | | | | |
|---|---|---|---|---|
| 8,900,240 | B2* | 12/2014 | White | A61B 17/7032 606/86 A |
| 9,198,692 | B1* | 12/2015 | Doose | A61B 17/7032 |
| 2005/0171540 | A1* | 8/2005 | Lim | A61B 17/7005 606/86 A |
| 2005/0192570 | A1 | 9/2005 | Jackson | |
| 2006/0069391 | A1* | 3/2006 | Jackson | A61B 17/7037 606/62 |
| 2006/0111713 | A1* | 5/2006 | Jackson | A61B 17/7037 606/914 |
| 2006/0149238 | A1* | 7/2006 | Sherman | A61B 17/7031 606/254 |
| 2008/0177269 | A1* | 7/2008 | Seelig | A61B 17/8866 606/90 |
| 2009/0171391 | A1* | 7/2009 | Hutton | A61B 17/7032 606/246 |
| 2009/0306721 | A1* | 12/2009 | Kirschman | A61B 17/7032 606/267 |
| 2010/0030283 | A1* | 2/2010 | King | A61B 17/7037 606/86 A |
| 2011/0184469 | A1* | 7/2011 | Ballard | A61B 17/7091 606/279 |
| 2011/0257692 | A1* | 10/2011 | Sandstrom | A61B 17/7085 606/86 A |
| 2012/0035668 | A1* | 2/2012 | Manninen | A61B 17/7037 606/305 |
| 2012/0109208 | A1* | 5/2012 | Justis | A61B 17/7032 606/264 |
| 2012/0271355 | A1* | 10/2012 | Steele | A61B 17/7008 606/264 |
| 2013/0018419 | A1* | 1/2013 | Rezach | A61B 17/7076 606/264 |
| 2013/0046352 | A1* | 2/2013 | McClintock | A61B 17/56 606/86 A |
| 2013/0096635 | A1* | 4/2013 | Wall | A61B 17/7085 606/305 |
| 2013/0289631 | A1* | 10/2013 | Jackson | A61B 17/7032 606/304 |
| 2014/0236236 | A1* | 8/2014 | Kruger | A61B 17/7037 606/267 |
| 2014/0330315 | A1* | 11/2014 | Butler | A61B 17/7085 606/278 |
| 2015/0066042 | A1* | 3/2015 | Cummins | A61B 17/7037 606/104 |
| 2015/0127053 | A1* | 5/2015 | Maruenda Paulino | A61B 17/708 606/267 |
| 2016/0030093 | A1* | 2/2016 | Walker | A61B 17/7086 606/275 |
| 2016/0113682 | A1* | 4/2016 | Altarac | A61B 17/7085 606/265 |

FOREIGN PATENT DOCUMENTS

| | | |
|---|---|---|
| JP | 2011-500267 A | 1/2011 |
| JP | 2013-078644 A | 5/2013 |
| WO | 2005/092218 A1 | 10/2005 |
| WO | 2007/149426 A2 | 12/2007 |
| WO | 2008/039247 A2 | 4/2008 |
| WO | 2009/055026 A1 | 4/2009 |
| WO | 2012/123655 A1 | 9/2012 |
| WO | 2013/034351 A1 | 3/2013 |

OTHER PUBLICATIONS

Chinese Office Action with English translation, Chinese Patent Application No. 201480032259.2, dated Feb. 28, 2017, 17 pgs.

* cited by examiner

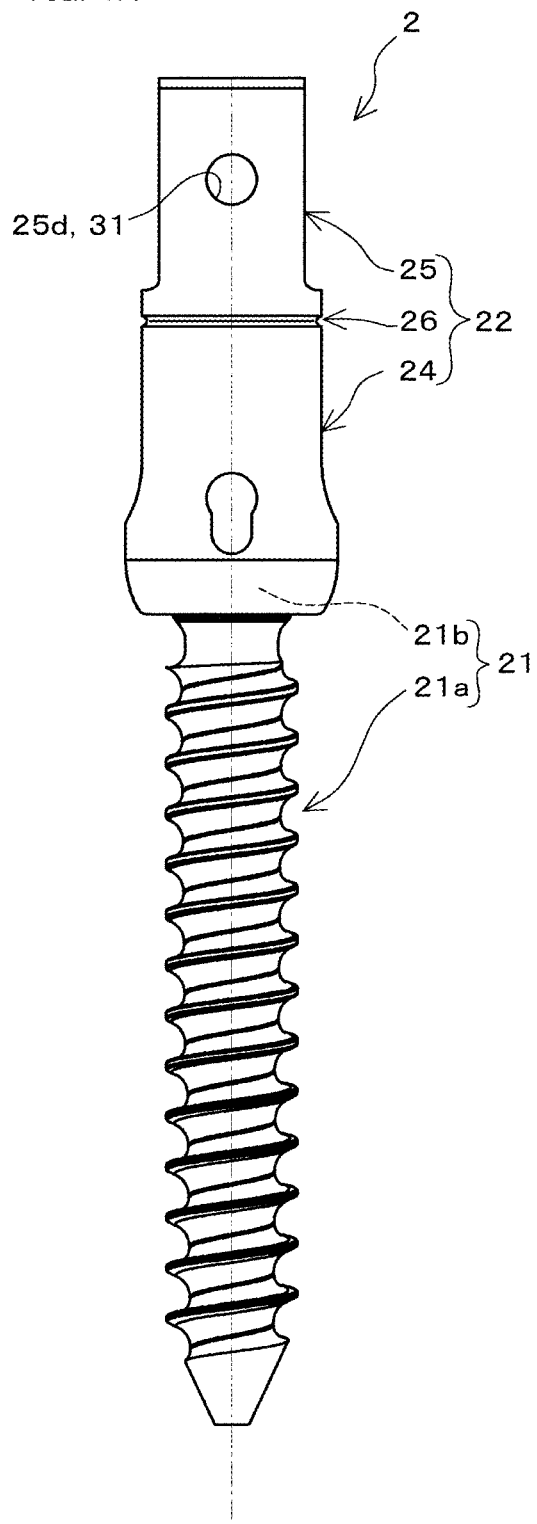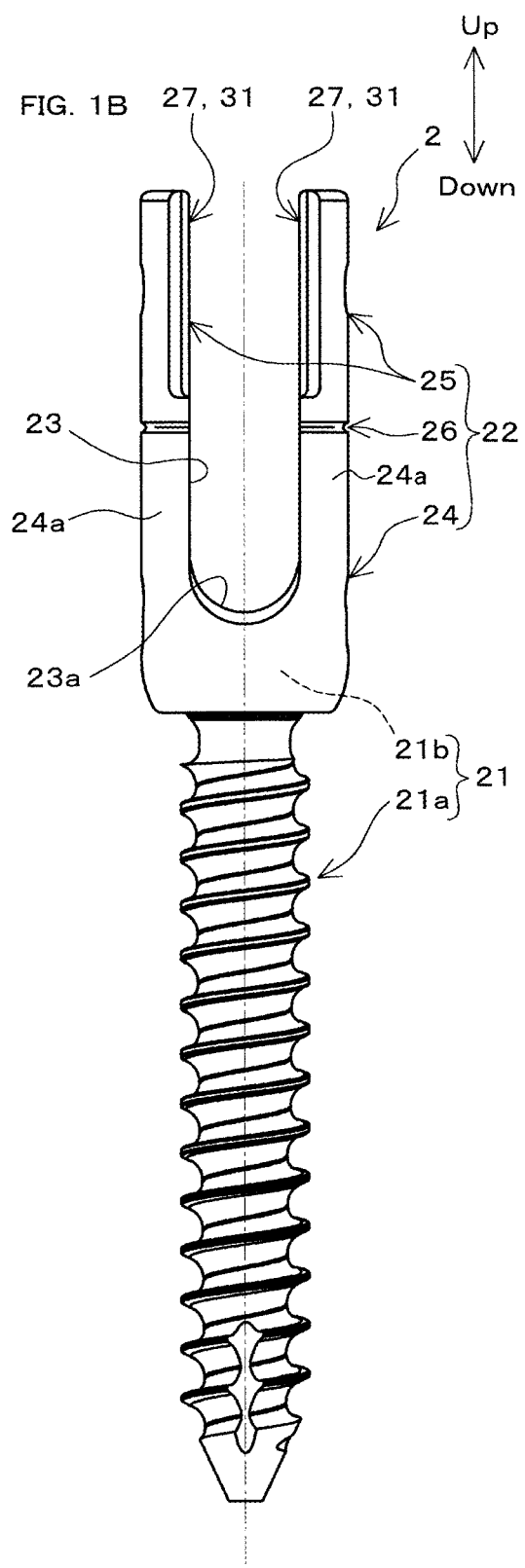

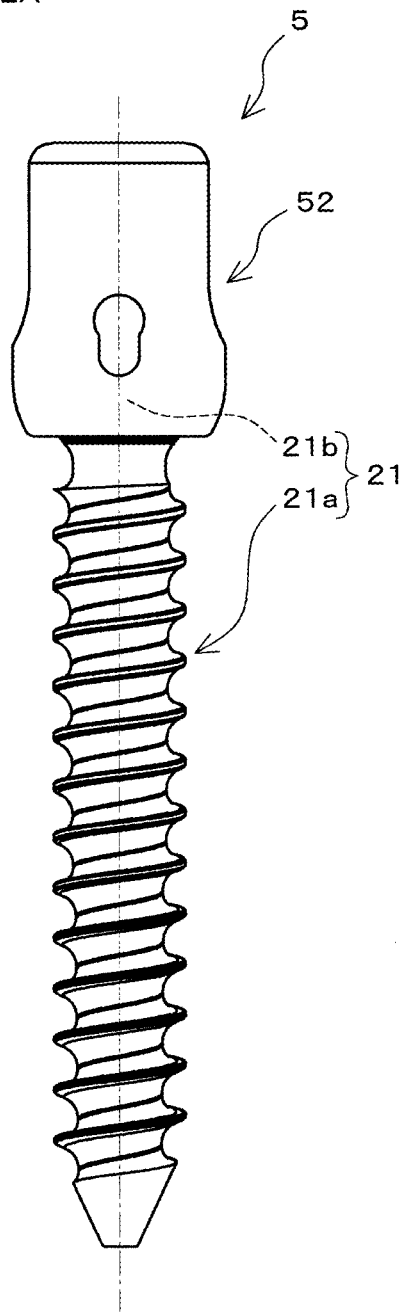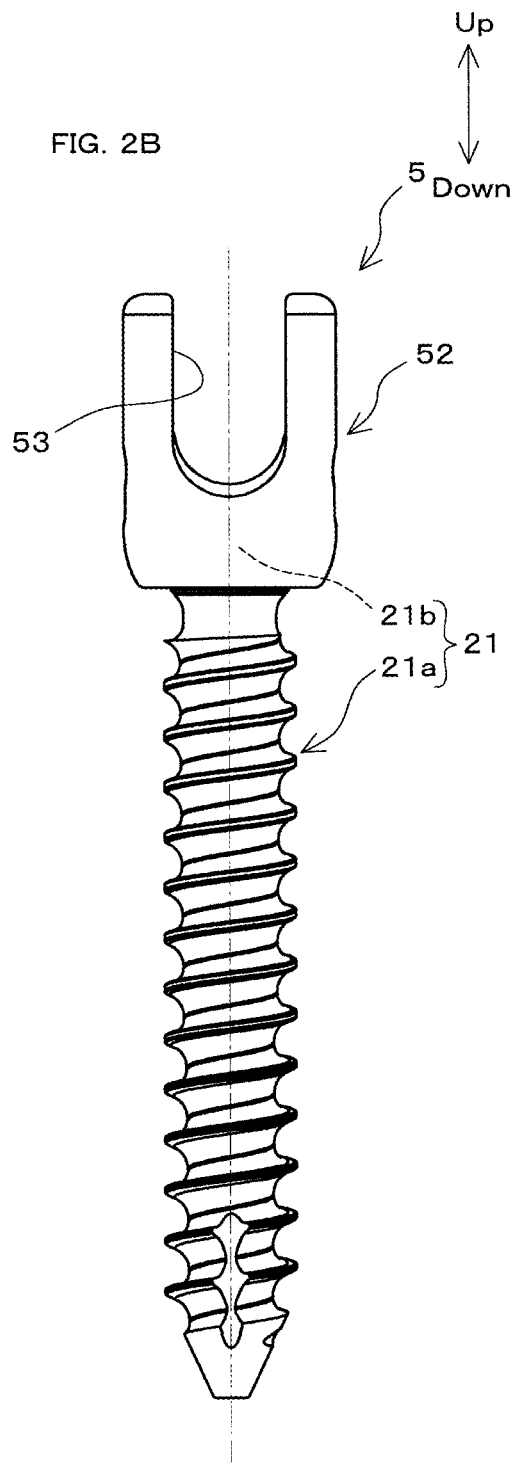

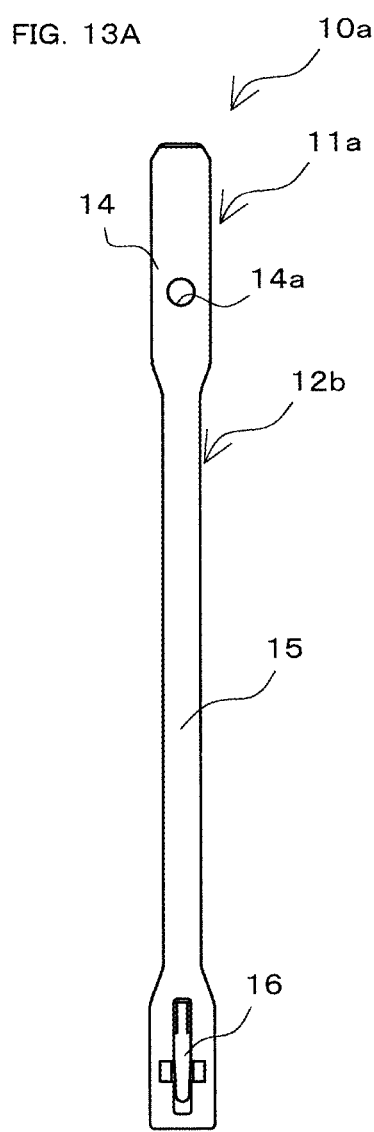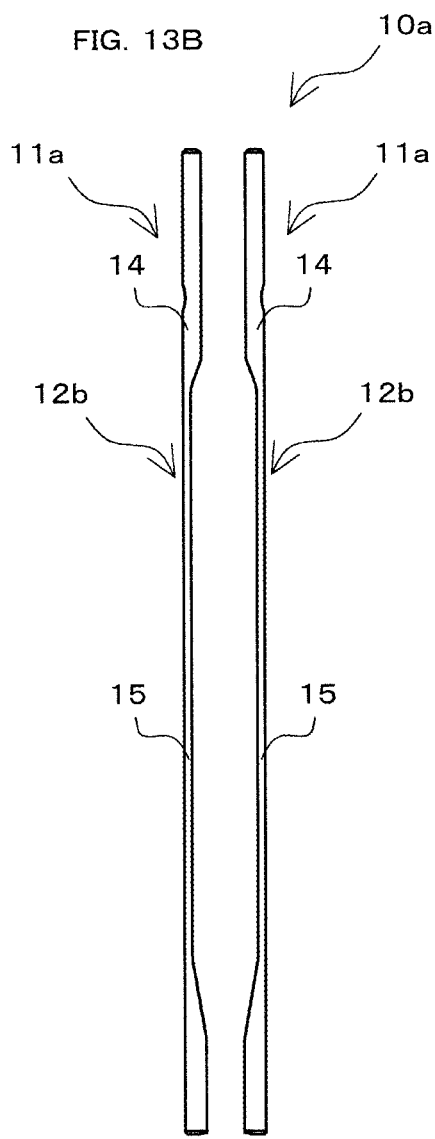

FIG. 16A
FIG. 16B
FIG. 16C
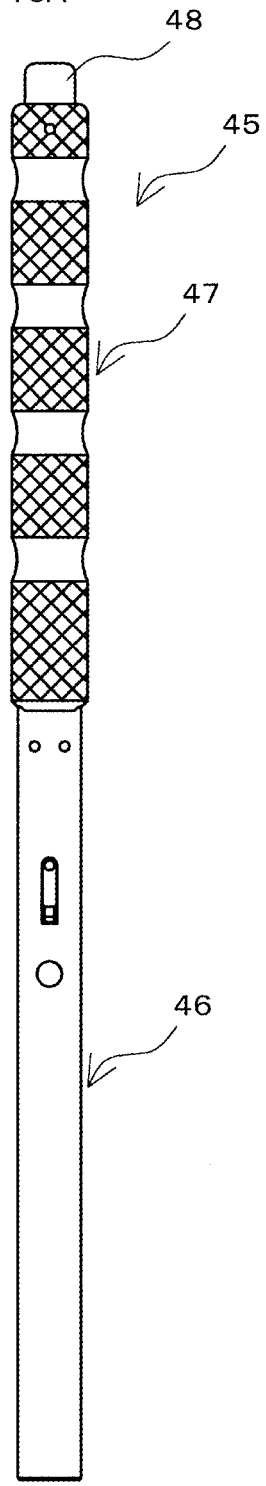
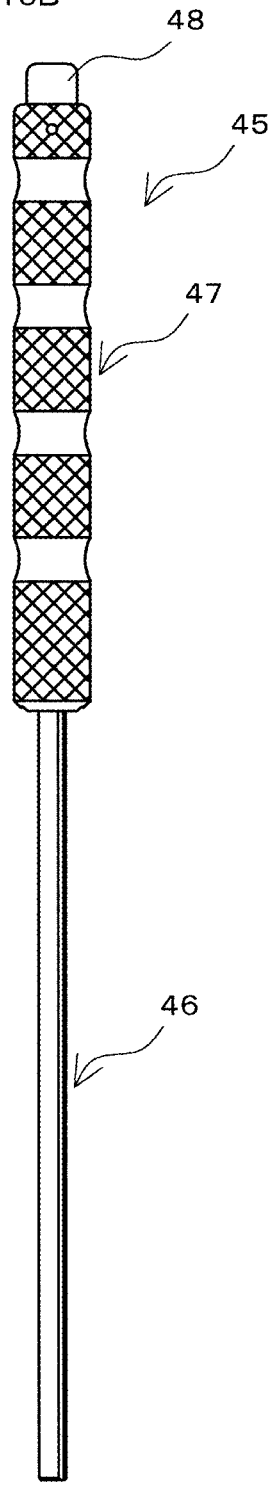
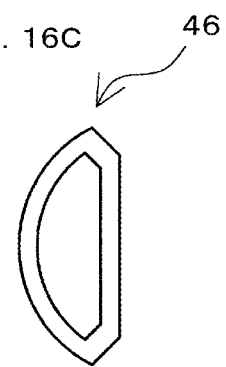

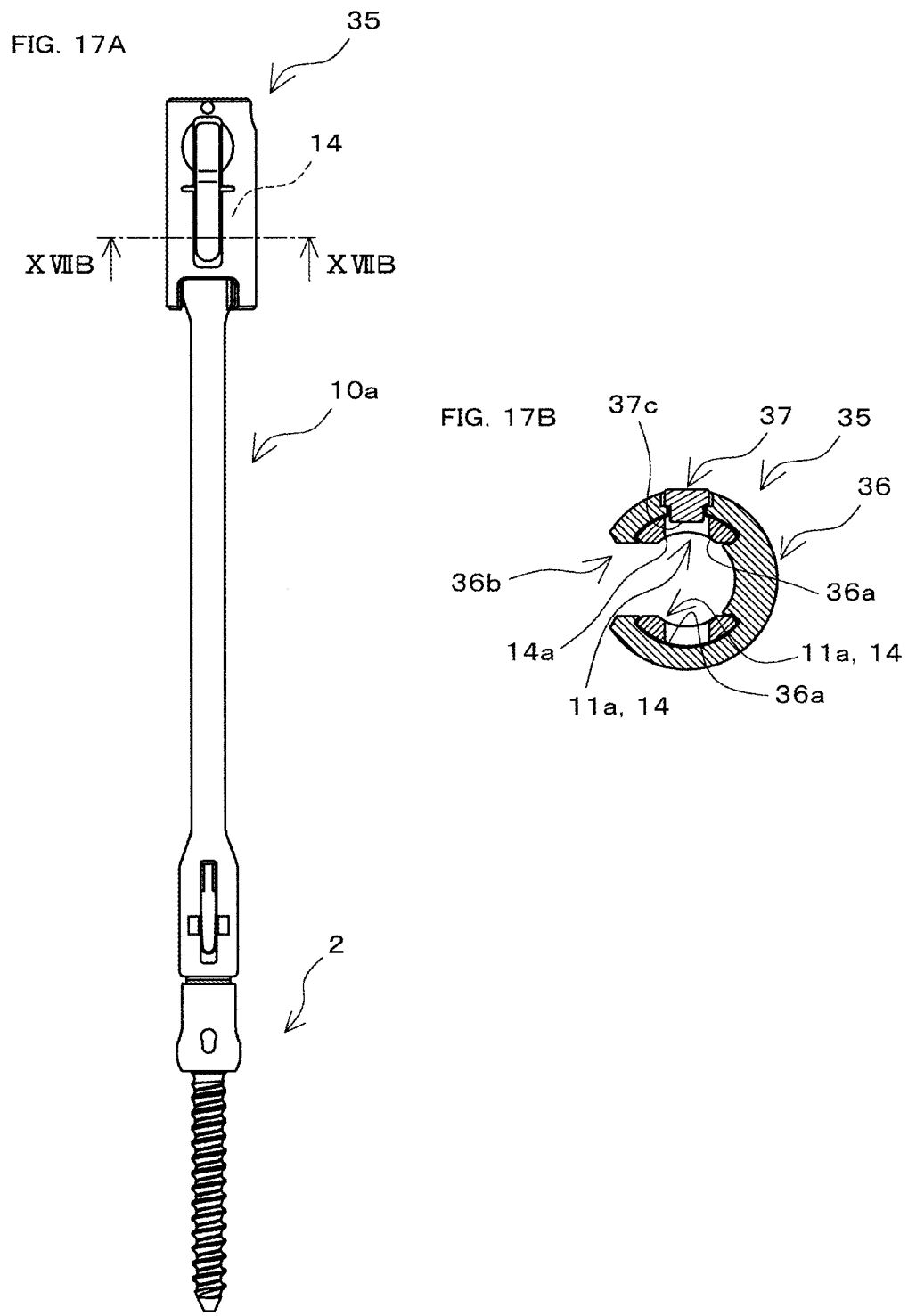

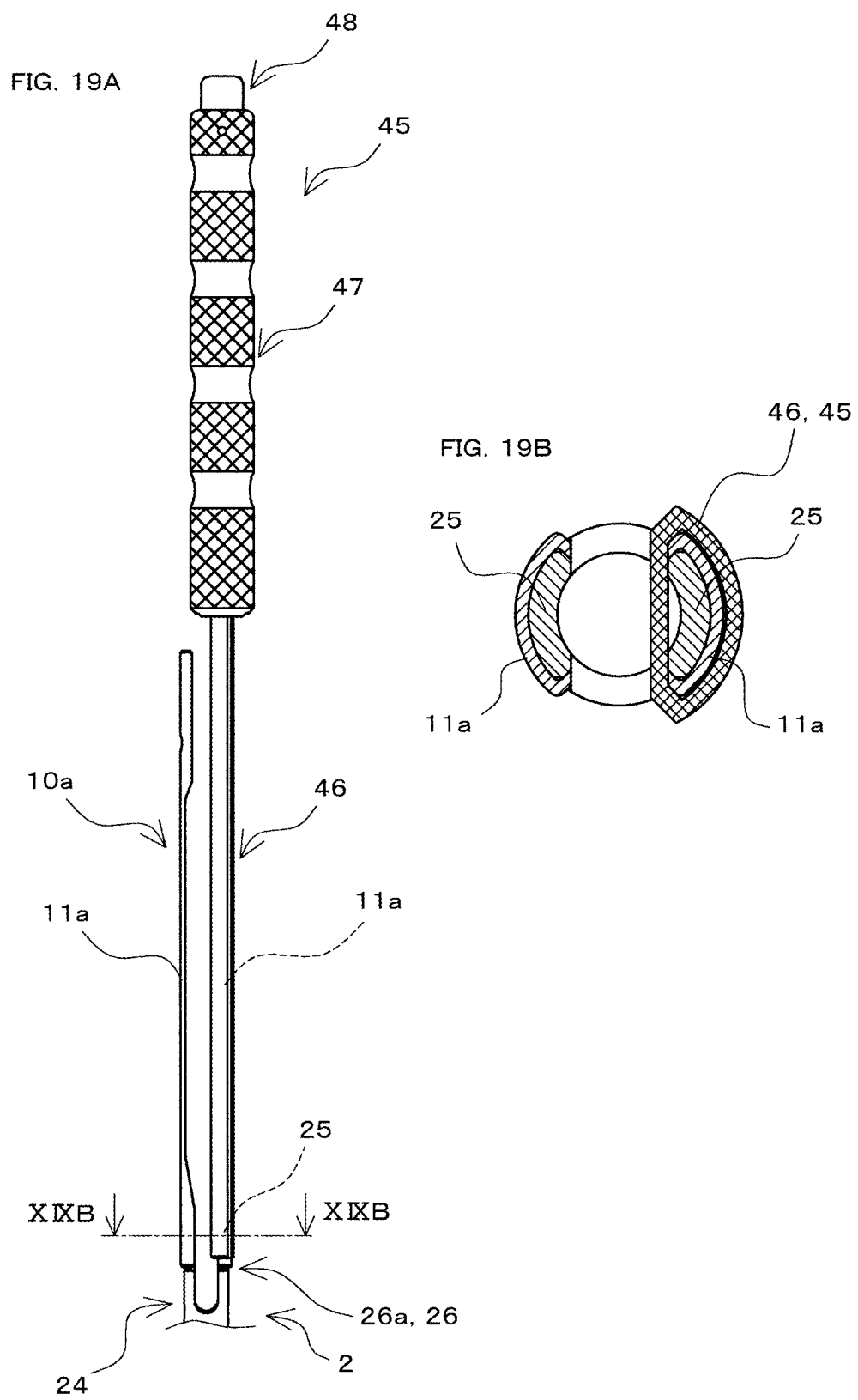

SPINAL IMPLANT AND DEVICE FOR SPINAL FIXING

CROSS-REFERENCE TO RELATED APPLICATION

This application is a U.S. National Stage entry of PCT Application No. PCT/JP2014/064745, filed on Jun. 3, 2014, which claims the benefit of priority from Japanese patent application No. 2013-120425, filed on Jun. 7, 2013, and Japanese patent application No. 2014-110280, filed on May 28, 2014, the disclosures of which are herein incorporated by reference in their entirety.

BACKGROUND OF THE INVENTION

1. Field of the Invention

The present invention relates to a spinal implant that is implanted in a spine to hold a fixing rod for fixing a plurality of vertebrae to each other, and a spine fixation device that is provided with the spinal implant.

2. Description of Related Art

Conventionally, a spine fixation device that is provided with a spinal implant configured to hold a fixing rod for fixing a plurality of vertebrae to each other, and an extender configured to guide the fixing rod to the spinal implant is known. With this spine fixation device, a plurality of implants are respectively implanted in the vertebrae, and then the fixing rod is inserted into slits in the implants using the extender and is fixed by setscrews. Accordingly, the plurality of vertebrae can be fixed to each other.

As the above-described spinal implant, JP 2009-540879A discloses, in FIGS. 1A and 1B, and the like thereof, a spinal screw assembly (100) (spinal implant) that includes a pedicle screw (102) and a body member (104) that is attached to a head part (105) of the pedicle screw (102). The body member (104) includes a tower portion (106), and a base body (108) to which the head part (105) of the pedicle screw (102) is attached. The body member (104) has a slot (130) into which a fixation rod (202) is inserted and that is formed to span from the base body (108) to the tower portion (106). The tower portion (106) is formed in a relatively elongated shape so as to be able to guide the fixation rod to the base body (108) externally from an incision in a patient. A break zone (110) for removing the tower portion (106) from the base body (108) is formed between the tower portion (106) and the base body (108).

Furthermore, JP 2011-500267A discloses a system (spine fixation device) that includes a screw implant (120) (spinal implant) and a screw extender device (100) (extender) that is engaged with the screw implant (120) (see FIGS. 1A and 1B, and the like of the patent document). In this system, a fixing rod is guided to the implant (120) by a channel (112) formed in the extender device (100). Then, the device (100) is removed from the implant (120) by a remover tool (800).

SUMMARY OF THE INVENTION

In JP 2009-540879A above, the tower portion that is removed after the fixation rod is attached to the implant is formed in an elongated shape, and thus the size of the member (tower portion) that is discarded after completion of an operation is relatively large.

Furthermore, in Patent Document 2 above, a separate device is needed when the extender is removed from the implant.

The present invention was made to solve the above-described problems, and an object thereof is to remove an extender for guiding a fixing rod to a predetermined position in a spinal implant from the spinal implant without using a separate device, and to reduce the loss of materials to be discarded.

(1) A spinal implant according to an aspect of the present invention for achieving the above-described object includes: a screw part having a screw body part configured to be implanted in a spine; and a head part that is attached to a portion on an opposite side of the screw part to the screw body part and has a slit into which a fixing rod for fixing a plurality of vertebrae is to be inserted, wherein the head part includes: a base part that is provided as a portion on the screw part side of the head part and in which the fixing rod inserted into the slit is held; and a pair of tab parts that are formed so as to extend from the base part to an opposite side to the screw part and face each other across the slit, the pair of tab parts have a tab part-side engagement part to be engaged by an extender-side engagement part that is formed on an extender that is configured to be attached to the pair of tab parts to guide the fixing rod to the slit, and a weak part is formed between the base part and the pair of tab parts, the weak part being configured to be broken by an external force from the extender engaged with the pair of tab parts and separate the pair of tab parts from the base part.

According to this configuration, the extender is attached to the pair of tab parts of the head part of the spinal implant, and then the screw part of the spinal implant is implanted in the spine. Accordingly, the fixing rod is guided by the extender to the slit formed in the head part of the spinal implant.

Furthermore, in this configuration, by fixing the fixing rod to the spinal implant and then applying an external force to the extender, it is possible to break the weak part and separate the pair of tab parts from the base part. Accordingly, the extender can be removed from the spinal implant without using a separate device. Moreover, since a separate member (extender) from the spinal implant is used to guide the fixing rod to the slit in the spinal implant, it is possible to make the length of the tab parts shorter than that of the tower portion (equivalent to the tab parts) disclosed in JP 2009-540879A above.

Therefore, according to this configuration, it is possible to remove the extender from the spinal implant without using a separate device, and to reduce the loss of materials to be discarded.

(2) Preferably, the tab part-side engagement part includes a slide guide part that is formed on the tab parts to enable a slide part formed on the extender to slide, and a receiving part that is formed on the tab parts and into which a protrusion of a spring of the extender is to fit.

According to this configuration, by sliding the slide part of the extender along the slide guide part formed on the tab parts and fitting the protrusion of the spring of the extender into the receiving part of the tab parts, it is possible to engage the extender with the tab parts. Accordingly, it is possible to engage the extender with the tab parts, with a relatively simple configuration.

(3) More preferably, the slide guide part is formed, so as to extend in a direction in which the tab parts extend, in a portion on both sides of the tab parts in a width direction, which is a direction orthogonal to the direction in which the tab parts extend, so as to enable the slide part of which two are formed on the extender to slide.

According to this configuration, two slide parts formed on the extender are respectively engaged with the slide guide parts formed on both side portions of the tab parts in the width direction while sliding with respect to the slide guide parts. Accordingly, the extender can smoothly slide with respect to the tab parts by being slid in the direction in which the tab parts extend, in the state in which the extender is positioned with respect to the width direction of the tab parts.

(4) Furthermore, in order to solve the above-described problem, a spine fixation device according to an aspect of the present invention includes: the spinal implant having any of the above-described features; and an extender that is configured to be attached to the pair of tab parts of the spinal implant to guide the fixing rod to the slit formed in the spinal implant.

According to this configuration, it is possible to provide a spine fixation device in which the extender can be removed from the spinal implant without using a separate device, and that can reduce the loss of materials to be discarded.

(5) Preferably, the extender includes a pair of guide members that include a pair of main body parts that are spaced from each other and guide the fixing rod to the slit via a gap between the pair of main body parts and an extender-side engagement part that is formed on each of the pair of main body parts to engage with the tab part-side engagement part formed on each of the pair of tab parts of the spinal implant.

According to this configuration, it is possible to operate the pair of guide members engaged with the pair of tab parts separately. It is thus possible to easily separate the tab parts from the base part.

(6) More preferably, the guide members are configured by members that are more elastically deformable than the weak part.

According to this configuration, even if an excessive external force is applied to the extender in the state of being attached to the spinal implant, the guide members of the extender will bend. Accordingly, even if a large external force is exerted on the extender during the operation for some reason, the tab parts can be prevented from being broken.

(7) More preferably, the spine fixation device further includes a tab remover that is configured by a member that is less elastically deformable than the guide members and the weak part, and is configured to separate the pair of tab parts from the base part by an external force being applied to the tab remover mounted on the extender to break the weak part.

According to this configuration, by mounting the tab remover on the extender and applying an external force to the tab remover, it is possible to separate the tab parts from the base part. It is thus possible to separate the extender that is more elastically deformable than the weak part, together with the tab parts, from the base part.

(8) Preferably, the main body parts of the extender each include: a base end part that is a portion on an opposite side of the main body part to the extender-side engagement part; and an intermediate part that is a portion of the main body part between the extender-side engagement part and the base end part, and the spinal fixation device further includes a cap that is configured to externally cover the pair of base end parts so as to restrict the pair of guide members from moving closer to or away from each other.

According to this configuration, it is possible to prevent the pair of base end parts of the pair of guide members from moving closer to or away from each other, without covering a gap (gap into which the fixing rod is inserted) between the pair of intermediate parts of the pair of guide members.

Accordingly, the fixing rod can be guided to the slit in the spinal implant via this gap, in the state in which, for example, the distance between the pair of guide members is maintained. Furthermore, according to this configuration, since the positions of the pair of guide members can be fixed with respect to each other, it is possible to reduce the risk of the guide members being bent due to an excessive external force being exerted on the guide members during the operation.

(9) Preferably, the main body parts of the extender each include: a base end part that is a portion on an opposite side of the main body part to the extender-side engagement part; and an intermediate part that is a portion of the main body part between the extender-side engagement part and the base end part, and the spinal fixation device further includes an extender guard that is configured to externally cover at least the pair of intermediate parts so as to restrict the pair of guide members from moving closer to or away from each other.

According to this configuration, since the positions of the pair of intermediate parts of the pair of guide members can be fixed with respect to each other, it is possible to reduce the risk of the guide member being bent due to an excessive external force being exerted on the guide members during the operation.

(10) Preferably, the tab part-side engagement part includes a slide guide part and a receiving part that are formed on the tab parts, and the extender-side engagement part includes a slide part formed on the main body parts so as to be able to slide with respect to the slide guide part, and a protrusion that is formed on a spring attached to the main body parts and is configured to fit into the receiving part formed on the tab parts.

According to this configuration, by sliding the slide part with respect to the slide guide part and fitting the protrusion of the spring into the receiving part of the tab parts, it is possible to engage the extender with the tab parts. Accordingly, with a relatively simple configuration, it is possible to engage the extender with the tab parts.

(11) More preferably, the slide part is formed so as to extend in the direction in which the fixing rod is guided in the extender, and the spring is formed so as to extend in the direction in which the slide part extends, and is provided as a blade spring that has the protrusion formed at one end and is fixed at the other end to the main body part.

According to this configuration, since a sufficient distance can be ensured between the fixed portion of the spring and the load point (protrusion), the load that is exerted on the spring can be reduced. Accordingly, the spring is unlikely to fail.

BRIEF DESCRIPTION OF THE DRAWINGS

FIG. 1A illustrates the shape of a reduction screw of a spine fixation device according to the present embodiment, with FIG. 1A being a front view.

FIG. 1B illustrates the shape of a reduction screw of a spine fixation device according to the present embodiment, with FIG. 1B being a side view.

FIG. 2A illustrates the shape of a standard screw, with FIG. 2A being a front view.

FIG. 2B illustrates the shape of a standard screw, with FIG. 2B being a side view.

FIG. 13A illustrates the shape of the extender shown in FIG. 12, with FIG. 13A being a front view.

FIG. 13B illustrates the shape of the extender shown in FIG. 12, with FIG. 13B being a side view.

FIG. 16A illustrates the shape of a tab remover shown in FIG. 12, with FIG. 16A being a front view.

FIG. 16B illustrates the shape of a tab remover shown in FIG. 12, with FIG. 16B being a side view.

FIG. 16C illustrates the shape of a tab remover shown in FIG. 12, with FIG. 16C being a diagram viewed in an arrow XVIC direction of FIG. 16A in which illustration of a grip part and a button is omitted.

FIG. 17A is a diagram illustrating a cap that is attached to the extender fixed to the reduction screw, together with the reduction screw and the extender.

FIG. 17B is a cross-sectional view taken along a line XVIIB-XVIIB of FIG. 17A.

FIG. 19A is a diagram illustrating the tab remover that is mounted on the extender fixed to the reduction screw, together with the reduction screw and the extender.

FIG. 19B is a cross-sectional view taken along a line XIXB-XIXB of FIG. 19A.

DETAILED DESCRIPTION OF THE INVENTION

Figure 3A:
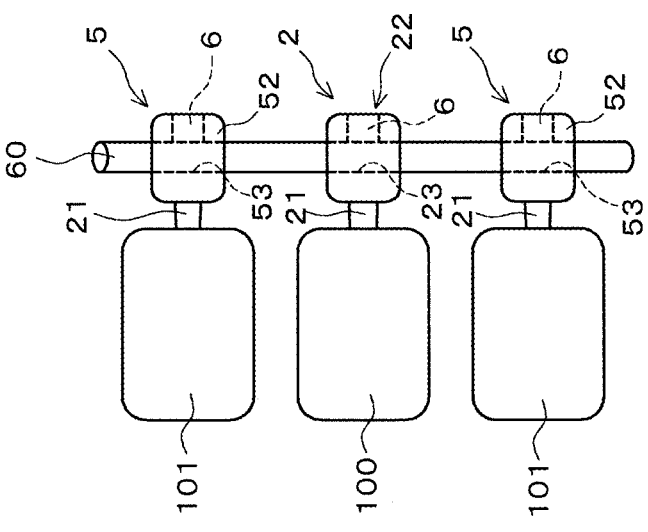
FIG. 3A schematically illustrates the operation when reduction is performed using the reduction screw shown in FIG. 1, with FIG. 3A being a diagram before reduction.

Hereinafter, embodiments for implementing the present invention will be described with reference to the drawings. The present invention is widely applicable to a spinal implant that is implanted in a spine to hold a fixing rod for fixing a plurality of vertebrae to each other, and a spine fixation device that is provided with the spinal implant.

A spine fixation device 1 according to the present embodiment is provided with a reduction screw 2 and an extender 10. The reduction screw 2 is used as a spinal implant for use in fixing a fixing rod 60 to adjacent vertebrae, the fixing rod 60 being for fixing the vertebrae to each other. The extender 10 is used to guide the fixing rod 60 to slits 23 in the reduction screw 2 when installing the fixing rod 60 is in the reduction screw 2.

The reduction screw 2 according to the present embodiment is used to perform a procedure known as reduction. Reduction is a treatment that is performed on a patient with spondylolisthesis to put a vertebra that has shifted forward relative to the other vertebrae back to the original position (to the back side). In order to perform this reduction, a standard screw 5, in addition to the above-described reduction screw 2, is ordinarily used. Similarly to the reduction screw 2, the standard screw 5 is used as a fixation implant for fixing the fixing rod 60 to the vertebrae.

[Schematic Configurations of Reduction Screw and Standard Screw]

FIG. 1 show a front view and a side view of the reduction screw 2, and FIG. 2 show a front view and a side view of the standard screw 5. As shown in FIGS. 1 and 2, the screws 2 and 5 include a screw part 21 and a head part 22 or 52. Note that in the following, for ease of description, the direction indicated by the "up" arrows in the drawings is referred to as the "upper side" or "upward", and the direction indicated by the "down" arrows is referred to as the "lower side" or "downward". Note that the vertical direction corresponds to the direction in which a screw body part 21a of the reduction screw 2 extends, or to the longitudinal direction of the extender 10.

The screw parts 21 of the screws 2 and 5 have the same configuration. The screw part 21 has the screw body part 21a and a screw head part 21b, which are integrally formed. The screw part 21 is a substantially rod-shaped member extending in the vertical direction, and threads are formed on the outer circumferential surface of the external screw body part 21a.

The head parts 22 and 52 are substantially tubular members in which two slits 23 and slits 53 are formed and that are formed so as to extend upward from the upper portion of the screw part 21. A female screw into which a setscrew 6 is to be screwed is formed on the inner periphery of the head parts 22 and 52. A through-hole (illustration thereof is omitted) is formed in the lower end part of the head parts 22 and 52.

In the screws 2 and 5, the screw body part 21*a* of the screw part 21 extends downward through the through-hole in the state in which the screw head part 21*b* is accommodated in the head parts 22 and 52. The lower side (screw body part 21*a* side) portion of the screw head part 21*b* is held so as to be rotatable with respect to the outer edge portion of the through-hole. Accordingly, the head parts 22 and 52 and the screw part 21 are rotatable with respect to each other.

The reduction screw 2 and the standard screw 5 have a different configuration in the following points. Specifically, the head part 22 of the reduction screw 2 is formed so as to have a length in the tube axis direction that is longer than that of the standard screw 5. Furthermore, the slits 23 in the reduction screw 2 are formed so as to have a length in the tube axis direction that is longer than the slits 53 in the standard screw 5. The detailed configuration of the reduction screw 2 will be described later.

Figure 3B:
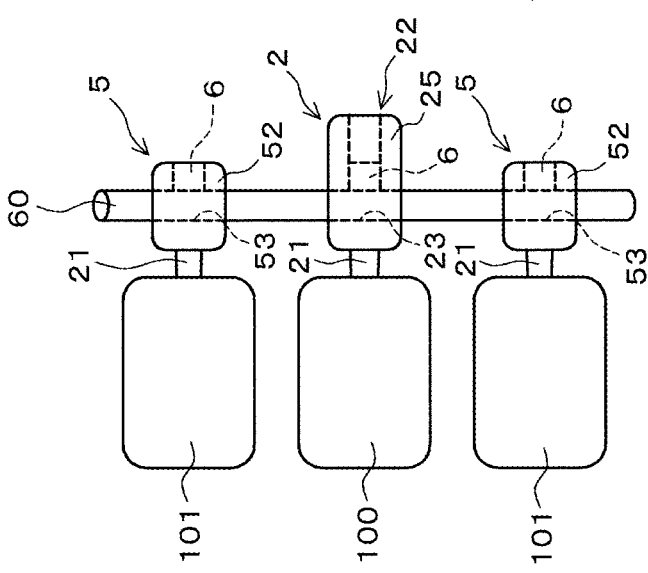
FIG. 3B schematically illustrates the operation when reduction is performed using the reduction screw shown in FIG. 1, with FIG. 3B being a diagram after reduction.
Figure 3C:
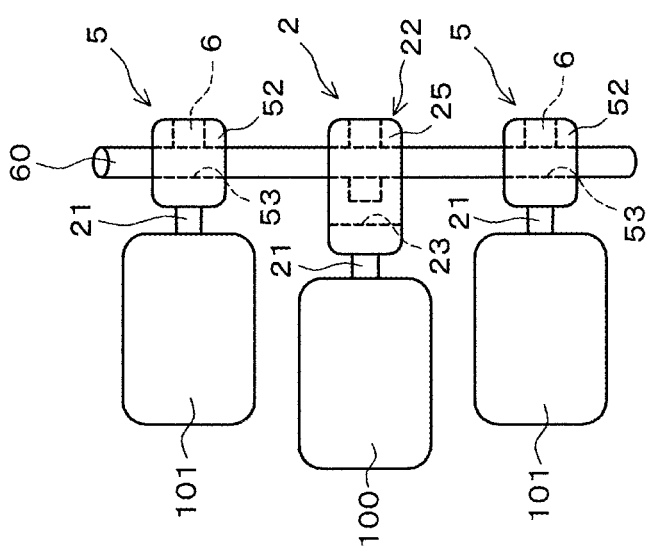
FIG. 3C schematically illustrates the operation when reduction is performed using the reduction screw shown in FIG. 1, with FIG. 3C being a diagram showing a state in which tab parts of the reduction screw are separated after reduction.

FIG. 3 schematically illustrate the operation when reduction is performed using the reduction screw 2 according to the present embodiment, with FIG. 3A being a diagram showing the state before reduction, and FIG. 3B being a diagram showing the state after reduction. The procedure when reduction is performed will be described with reference to FIG. 3. Three vertebrae shown in FIG. 3 are an affected area of a patient with spondylolisthesis, and include a vertebra 100 that has shifted forward, and two vertebrae 101 adjacent to the vertebra 100. The vertebra 100 is a vertebra that is to be subjected to reduction.

First, an operator makes an incision in the back or the like of the patient, and then the reduction screw 2 and the standard screws 5 are implanted by being screwed in the vertebrae 100 and 101. Specifically, the operator implants the standard screws 5 into the vertebrae 101, and implants the reduction screw 2 into the vertebra 100. Then, the operator inserts the fixing rod 60 into the slits 23 and 53 formed in the screws 2 and 5, and then screws the setscrew 6 into the head part 52 of the standard screws 5. Accordingly, the fixing rod 60 is held by being sandwiched between the head parts 52 and the setscrews 6, and thus the fixing rod 60 is fixed between the two vertebrae 101 (see FIG. 3A). Note that at this time, as shown in FIG. 3A, the fixing rod 60 is positioned at portions on the front end side (portions of the slits 23 on the opposite side to the screw part 21) of the slits 23 of the reduction screw 2.

In the above-described state, the reduction is performed. Specifically, the operator sets the setscrew 6 at the front end part (portion of the head part 22 on the opposite side to the screw part 21) of the head part 22 of the reduction screw 2, and screws in the setscrew 6. Accordingly, the vertebra 100, together with the reduction screw 2, is pulled to the fixing rod 60 side (see FIG. 3B). It is thus possible to pull the vertebra 100 to the back side and move it to a desired position.

Note that in the reduction screw 2 according to the present embodiment, upper end side portions (tab parts 25) of the head part 22 are removed, after reduction is performed as described above (see FIG. 3C), detail of which will be described later. Accordingly, the portion of the head part 22 of the reduction screw 2 that protruded above the standard screw 5 is eliminated, and thus it is possible to reduce the parts that remain in the body.

Detailed Configuration of Reduction Screw

As described above, the reduction screw 2 has, as shown in FIG. 1, the screw part 21 and the head part 22. Also, the head part 22 of the reduction screw 2 according to the present embodiment has a base part 24, a pair of tab parts 25, and a weak part 26, which are integrally formed.

The base part 24 is provided as a portion on the screw part 21 side (lower side of FIG. 1) of the head part 22. The upper portions of the base part 24 are provided as a pair of opposed walls 24*a*. The lower portions of the slits 23 are formed between the pair of opposed walls 24*a*.

The pair of tab parts 25 is provided as parts (upper side of FIG. 1) on the opposite side of the head part 22 to the screw part 21. Each tab part 25 is formed in the shape of a piece extending upward from the corresponding opposed wall 24*a*. The upper portions of the slits 23 are formed between the pair of tab parts 25.

Figure 4A:
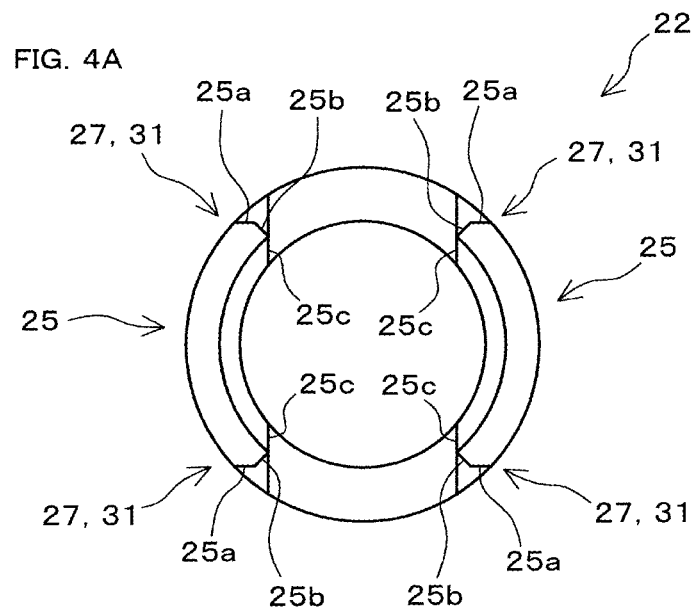
FIG. 4A illustrates the shape of a head part of the reduction screw shown in FIG. 1, with FIG. 4A being a plan view.
Figure 4B:
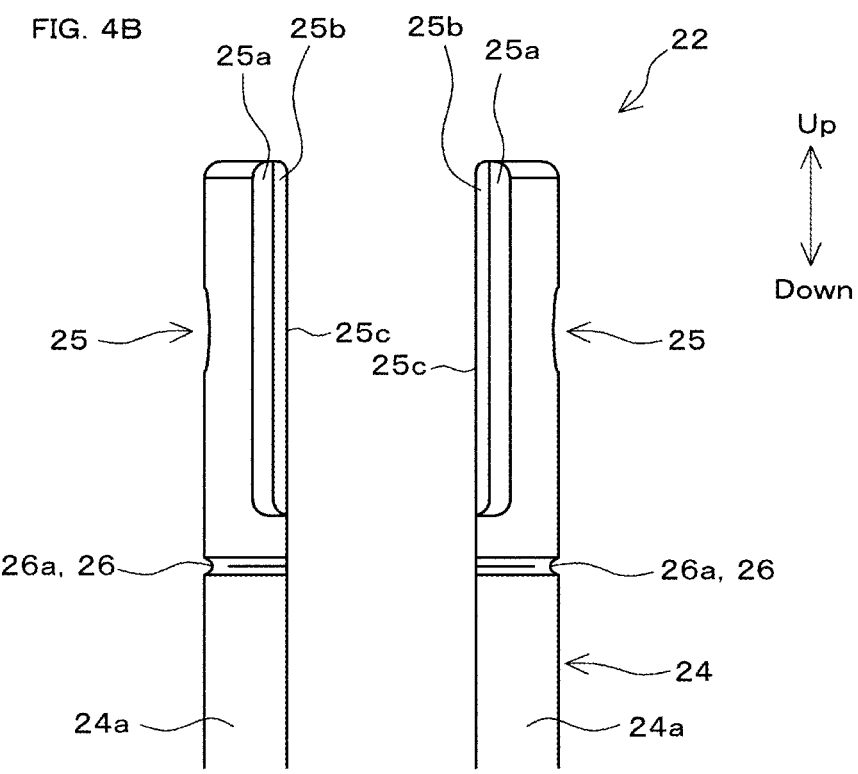
FIG. 4B illustrates the shape of a head part of the reduction screw shown in FIG. 1, with FIG. 4B being an enlarged view of a part of the head part.

FIG. 4A is a plan view of the head part 22, and FIG. 4B is an enlarged view of the upper portion (tab parts) of the head part 22. A slide guide part 27 is formed on both side portions of each tab part 25 in the width direction (direction that is orthogonal to the direction in which the tab part 25 extends, and that is the direction in which the fixing rod 60 extends in a state in which the fixing rod 60 is inserted in the head part 22). The slide guide part 27 is configured such that a slide part 13 of the extender 10 is engaged therewith, details of which will be described later.

The slide guide part 27 has a guide face 25*b*. The guide face 25*b* is configured by a chamfered part that is formed in a portion at which an end face 25*a* in the width direction of the tab part 25 intersects with a slit face 25*c*, which is a face constituting the slit 23 in the tab part 25. As shown in FIG. 4A, the pair of guide faces 25*b* formed on each tab part 25 are formed so as to approach each other from the outside to the inside in the radial direction of the head part 22 when seen in a plan view. Furthermore, as shown in FIG. 4B, the guide face 25*b* is formed so as to extend downward to in front of the weak part 26 from the upper end of the tab part 25.

Furthermore, as shown in FIG. 1, each tab part 25 has a hole 25*d*. The hole 25*d* is formed by a through-hole that passes through the tab part 25 in the thickness direction. This hole 25*d* is provided as a receiving part into which fits a protrusion 17 formed on a spring 16 of the extender 10.

The slit 23 is formed so as to extend in the vertical direction across the base part 24 and the tab part 25. As shown in FIG. 4A, two slits 23 are formed so as to oppose each other. Each slit 23 is provided extending downward from the upper end of the tab part 25 to an intermediate portion in the vertical direction of the base part 24. The lower end of the slit 23 is formed as a semicircular arc part 23*a*. This arc part 23*a* is formed such that the fixing rod 60 fits therein.

The weak part 26 is formed between the base part 24 and each tab part 25 of the head part 22. The weak part 26 is configured to be less robust than other portions of the head part 22, so as to be broken by application of an external force to the tab part 25. In the present embodiment, the weak part 26 is provided as a pair of groove parts 26*a* that extend in the circumferential direction of the outer circumferential surface of the head part 22. Each groove part 26*a* is formed between one of the opposed walls 24*a* and the tab part 25 provided correspondingly to this opposed wall 24*a*. Accordingly, the weak part 26 is thinner than the portions (opposed walls 24*a* and the tab parts 25) of the head part 22 in the vicinity of the weak part 26. The weak part 26 is configured to be broken by application of a predetermined external force to the tab parts 25 in the state in which the screw part 21 is implanted in a vertebra, and to thereby separate the tab parts 25 from the base part 24.

[Extender Configuration]

The extender 10 is used to insert the fixing rod 60 into the slits 23 of the reduction screw 2 attached to the vertebra 100. Using the extender 10, it is possible to reliably guide the fixing rod 60 to the slits 23 of the reduction screw 2 and to ensure the visibility of the operator.

Figure 5:
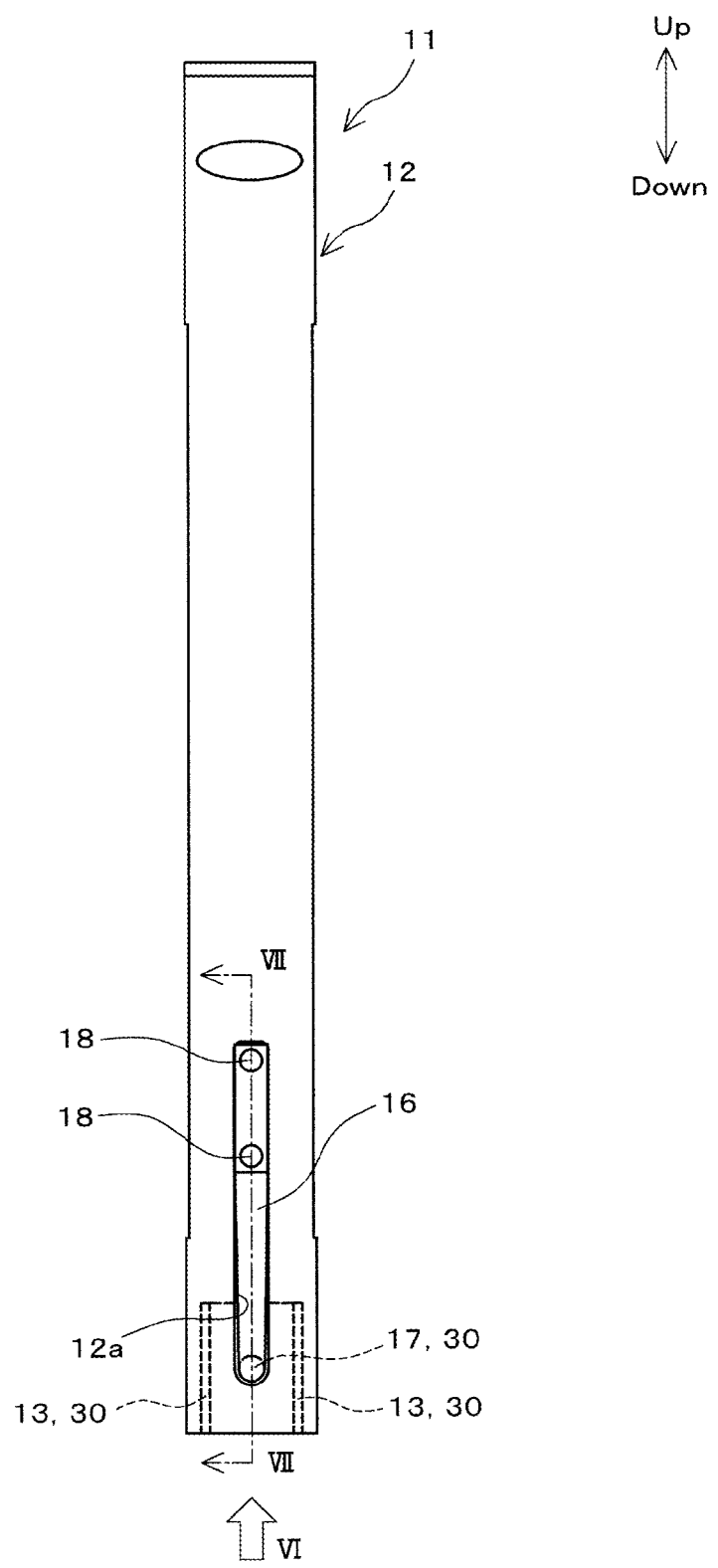
FIG. 5 is a front view of a blade of an extender of the spine fixation device according to the present embodiment.
Figure 6:
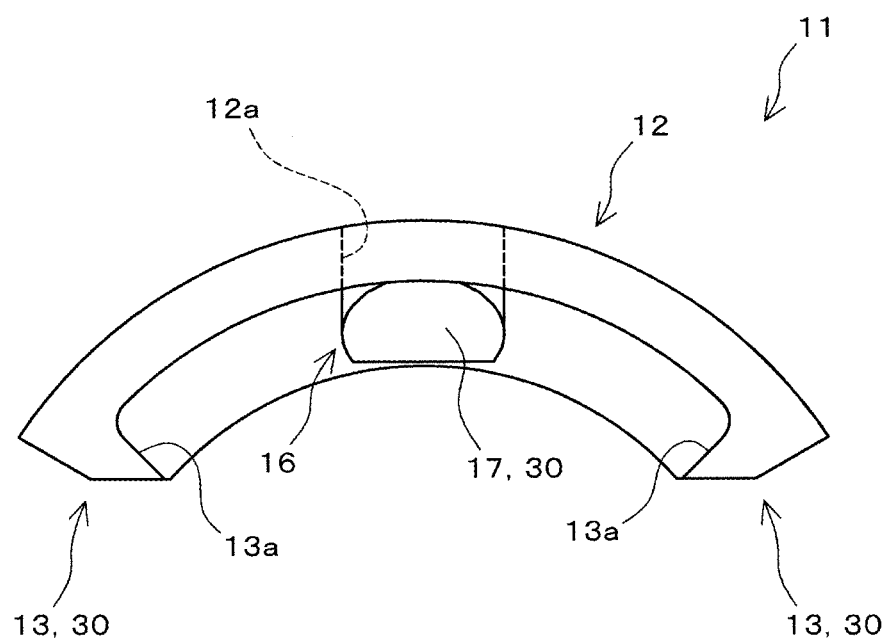
FIG. 6 is a diagram illustrating the blade shown in FIG. 5 as viewed in an arrow VI direction.
Figure 7:
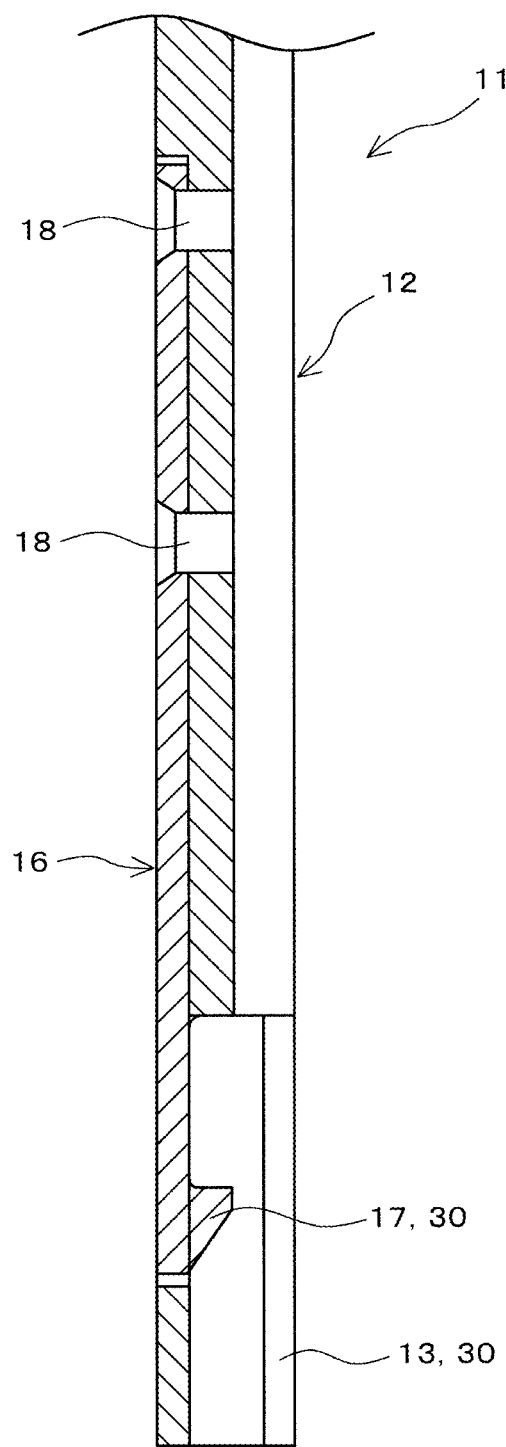
FIG. 7 is a cross-sectional view taken along a line VII-VII of FIG. 5.

FIGS. 5 to 7 are diagrams illustrating the shape of one of two blades 11 (guide members) constituting the extender 10, with FIG. 5 being a front view of the blade 11, FIG. 6 being a diagram in which the blade 11 is viewed in the direction of the arrow VI of FIG. 5, and FIG. 7 being a cross-sectional view of the blade 11 taken along the line VII-VII of FIG. 5. The extender 10 according to the present embodiment has two blades 11 that have the same shape.

Each blade 11 has an elongated member 12 (main body part), and the spring 16.

The elongated member 12 is an elongated member formed so as to have a substantially arc-like cross-section. The elongated member 12 is made from a metal material such as stainless steel, for example. The elongated member 12 has a long hole 12a, which extends in the longitudinal direction, in a portion on one side (lower side of FIG. 5) in the longitudinal direction thereof. The long hole 12a passes through the elongated member 12 in the thickness direction thereof. The spring 16 is arranged in this long hole 12a.

The elongated member 12 has a pair of slide parts 13. The pair of slide parts 13 are formed in both end portions of the elongated member 12 on the lower side (side on which the long hole 12a is formed) in the width direction so as to extend upward from the lower end of the elongated member 12. Furthermore, as shown in FIG. 6, the slide parts 13 project inward in the radial direction of the elongated member 12. The slide parts 13 are configured so as to be able to be engaged with and slide with respect to the slide guide parts 27 of the reduction screw 2.

Each slide part 13 has a slide face 13a. The slide faces 13a are respectively configured by inner faces of the pair of slide parts 13. As shown in FIG. 6, the slide faces 13a are formed so as to approach each other from the outside to the inside in the radial direction. The slide faces 13a are formed so as to be able to slide with respect to the guide faces 25b of the reduction screw 2 in the longitudinal direction of the blade 11.

The spring 16 is configured by a blade spring formed in the shape of an elongated blade. The spring 16 is arranged along the long hole 12a on the radially outward side of the elongated member 12. Specifically, in the state in which a portion on one end side (lower side of FIG. 5) of the spring 16 is exposed on the inner circumferential side of the elongated member 12 via the long hole 12a, a portion on the other end side of the spring 16 is fastened to the elongated member 12 by two screws 18. Furthermore, the protrusion 17 is formed on the front end portion (lower side of FIG. 5) of the spring 16. This protrusion 17 protrudes inward in the radial direction of the elongated member 12 via the long hole 12a. This protrusion 17 is formed so as to fit into the hole 25d of the corresponding tab part 25.

[Engagement Mechanism]

Figure 8:
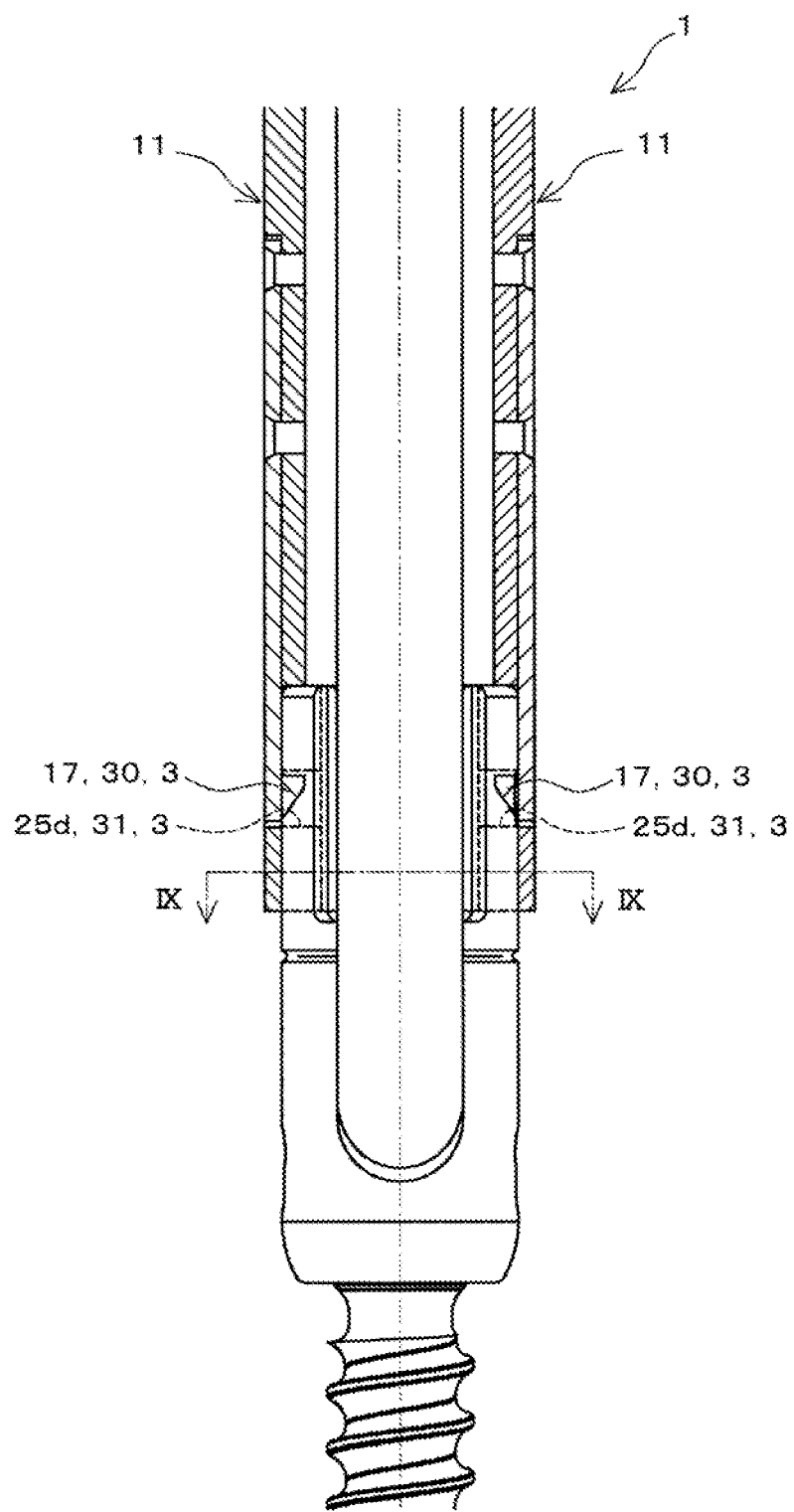
FIG. 8 is a diagram illustrating a state in which the extender is engaged with the reduction screw, with the extender being shown in cross-section.
Figure 9:
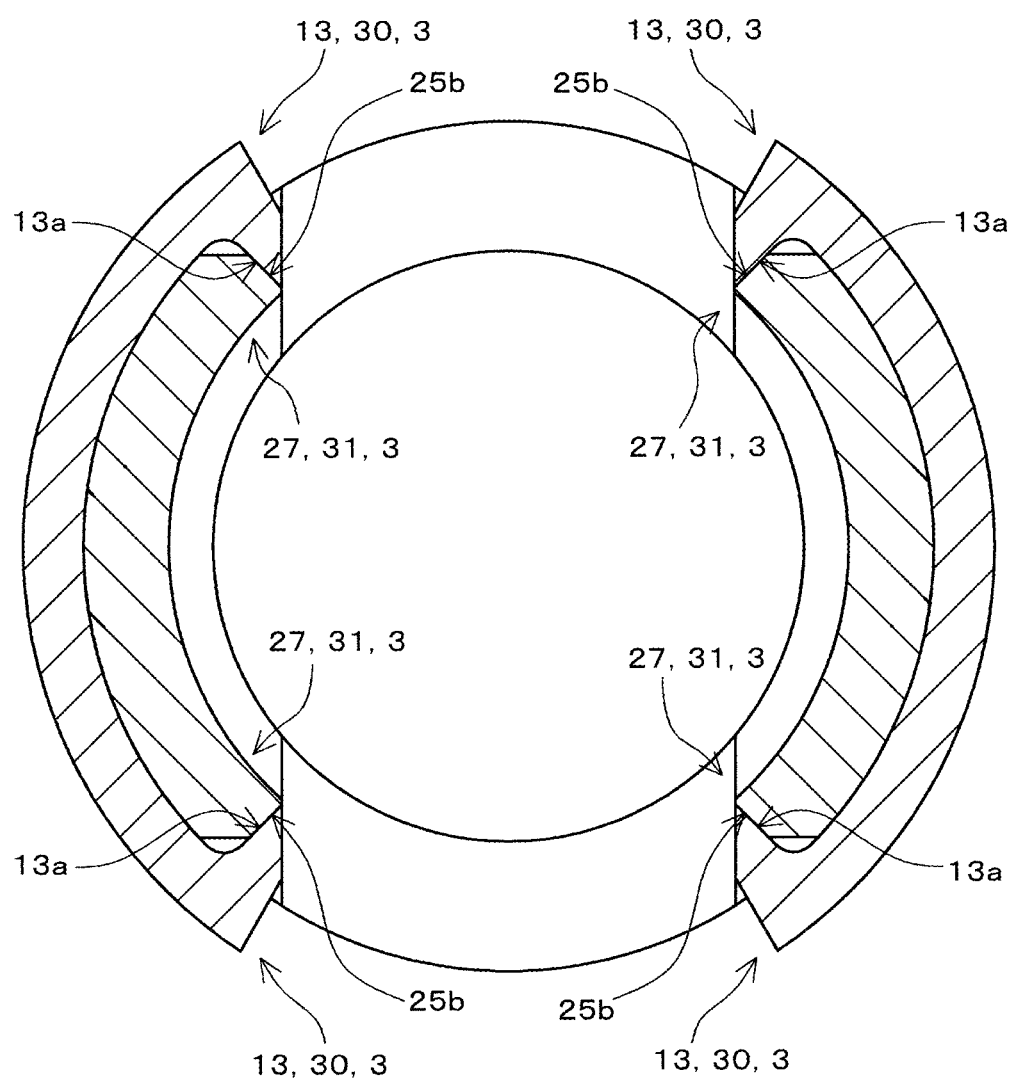
FIG. 9 is a cross-sectional view taken along a line IX-IX of FIG. 8.

FIGS. 8 and 9 are diagrams illustrating the state in which the reduction screw 2 and the extender 10 are engaged with each other. The spine fixation device 1 according to the present embodiment includes an engagement mechanism 3. The engagement mechanism 3 includes a tab part-side engagement part 31, which is formed on the tab part 25, and an extender-side engagement part 30, which is formed on the extender 10. The tab part-side engagement part 31 includes the above-described hole 25d and slide guide parts 27. The extender-side engagement part 30 includes the above-described slide parts 13 and protrusion 17. The engagement mechanism 3 is configured such that the slide parts 13 and the slide guide parts 27 engage with each other and the protrusion 17 engages with the hole 25d.

[Reduction Procedure]

The procedure when reduction is performed using the above-described reduction screw 2 and extender 10 will be described below with reference to FIG. 3 and the like.

First, the operator makes an incision the back or the like of the patient, and then, as shown in FIG. 3, implants the reduction screw 2 into the vertebra 100 that has slipped forward using a driver (illustration thereof is omitted) or the like and implants the standard screws 5 into the adjacent two vertebrae 101.

At this time, the operator inserts the reduction screw 2 into the affected area in the state in which the extender 10 is engaged with the reduction screw 2. Specifically, the operator first arranges the lower end portion (lower portion of FIG. 5) of one blade 11 so that it faces the upper end portion of one tab part 25 (upper portion of FIG. 1), and moves the blade 11 toward the reduction screw 2 so that the tab part 25 is sandwiched between the pair of slide parts 13. At this time, the slide faces 13a slide with respect to the guide faces 25b, and then the protrusion 17 of the spring 16 of the blade 11 fits into the hole 25d of the tab part 25. Accordingly, the extender-side engagement part 30 (the slide parts 13 and the protrusion 17) is engaged with the tab part-side engagement part 31 (the slide guide parts 27 and the hole 25d), and thereby the blade 11 is fixed to the one tab part 25. Similarly, the operator engages the extender-side engagement part 30 of the other blade 11 into the tab part-side engagement part 31 of the other tab part 25, and thereby fixes this blade 11 to the other tab part 25. After having engaged the extender 10 with the reduction screw 2 in this manner, the operator inserts the reduction screw 2 into the affected area, and then implants the reduction screw 2 into the vertebra 100 using a driver or the like.

Then, the operator inserts the fixing rod 60 into a gap formed between the pair of blades 11 fixed to the reduction screw 2, and moves the fixing rod 60 to the reduction screw 2 side (patient side) so that the fixing rod 60 is inserted into the slits 23 of the screw 2 and the slits 53 of the screws 5 shown in FIG. 3.

Then, the operator fixes the fixing rod 60 between the two standard screws 5 (see FIG. 3A), by screwing setscrews 6 into the head parts 52 of the standard screws 5. In this state, the operator performs reduction by setting and fastening a setscrew 6 into the front end portion of the head part 22 of the reduction screw 2, and pulling the vertebra 100 to the fixing rod 60 side (to the back side) (see FIG. 3B).

Figure 10:
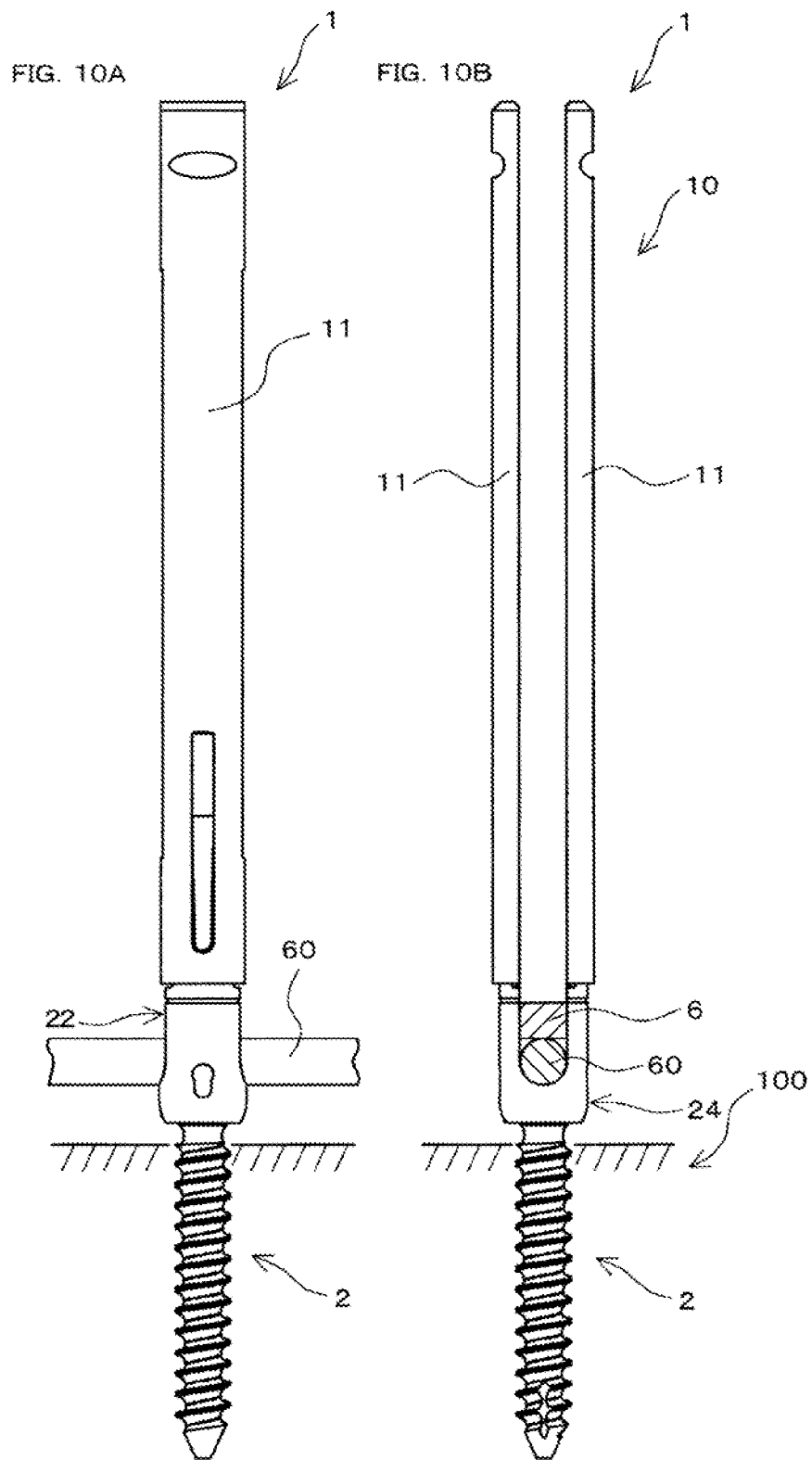
FIG. 10A illustrates states of the spine fixation device, a fixing rod, and a setscrew after reduction, with FIG. 10A being a front view.
FIG. 10B illustrates states of the spine fixation device, a fixing rod, and a setscrew after reduction, with FIG. 10B being a side view.

FIG. 10 is a diagram illustrating the states of the spine fixation device 1, the fixing rod 60, and the setscrew 6 after reduction. As shown in FIG. 10, after reduction, the fixing rod 60 and the setscrew 6 are fixed to the base part 24 of the head part 22 of the reduction screw 2.

Figure 11:
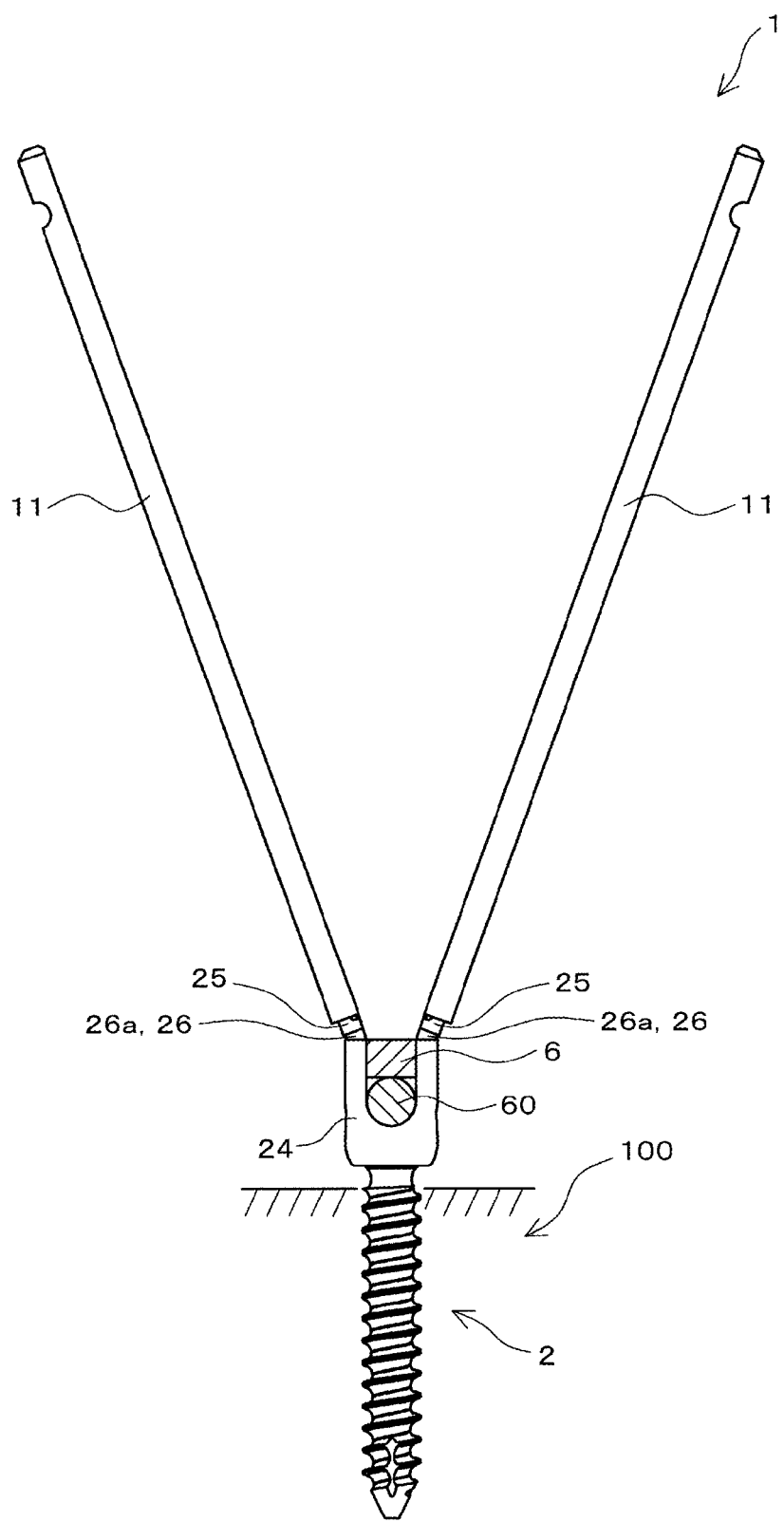
FIG. 11 is a diagram illustrating the operation of the extender when the tab parts of the reduction screw are broken off.

FIG. 11 is a diagram illustrating the operation when the tab parts 25 of the reduction screw 2 are separated from the base part 24 after reduction. As shown in FIG. 11, the operator applies, to the respective blades 11 engaged with the tab parts 25, an external force in the directions perpendicular to the longitudinal direction of the blades 11, and thereby breaks off the tab parts 25 at the groove parts 26a, which are provided as the weak part 26. Accordingly, the tab parts 25 engaged with the blades 11 are separated from the base part 24, and the portions (tab parts 25) of the reduction screw 2 that protrude upward from the standard screws 5 are removed (see FIG. 3C). Accordingly, the tab parts 25, which are no longer needed after reduction, can be removed from the body. Note that the operator may set a predetermined jig (not shown) for the blades 11, and operates the jig to apply an external force to the tab parts 25, and thereby separate the tab parts 25 from the base part 24.

[Effects]

As described above, by fixing the fixing rod 60 to the reduction screw 2 and then breaking the weak parts 26 by application of an external force to the extender 10, the pair of tab parts 25 of the reduction screw 2 according to the present embodiment can be separated from the base part 24. Accordingly, the extender 10 can be removed from the reduction screw 2 without using a separate device. Moreover, since a separate member (extender 10) from the spinal implant is used to guide the fixing rod 60 to the slits 23 of the reduction screw 2, it is possible to make the length of the tab parts 25 shorter than that of the tower portion (equivalent to the tab parts) disclosed in JP 2009-540879A above.

Therefore, with respect to the reduction screw 2, it is possible to remove the extender 10 from the reduction screw 2 without using a separate device, and to reduce the loss of the material to be discarded.

Furthermore, in the reduction screw 2, it is possible to engage the extender 10 with the tab parts 25, by sliding the slide parts 13 of the extender 10 along the slide guide parts 27 formed on the tab parts 25 and fitting the protrusions 17 of the springs 16 of the extender 10 into the holes 25d of the tab parts 25. Accordingly, it is possible to engage the extender 10 with the tab parts 25 with a relatively simple configuration.

Furthermore, in the reduction screw 2, two slide parts 13 formed on each blade 11 of the extender 10 are respectively engaged with the slide guide parts 27 formed on both side portions of the tab part 25 in the width direction while sliding with respect to the slide guide parts 27. Accordingly, the blades 11 can smoothly slide with respect to the tab parts 25 by being slid in the direction in which the tab parts 25 extend, in the state in which the blades 11 are positioned with respect to the width direction of the tab parts 25.

Furthermore, in the above-described embodiment, it is possible to provide the spine fixation device 1 in which the extender 10 can be removed from the reduction screw 2 without using a separate device, and the loss of the material to be discarded can be reduced.

Furthermore, in the spine fixation device 1, it is possible to operate the pair of blades 11 engaged with the pair of tab parts 25 separately. It is thus possible to easily separate the tab parts 25 from the base part 24.

Furthermore, in the spine fixation device 1, it is possible to engage the extender 10 with the tab parts 25 by sliding the slide parts 13 with respect to the slide guide parts 27 and fitting the protrusions 17 of the springs 16 into the holes 25d of the tab parts 25. Accordingly, it is possible to engage the extender 10 with the tab parts 25 with a relatively simple configuration.

Furthermore, in the spine fixation device 1, since a sufficient distance can be ensured between the fixed portion of the spring 16 and the load point (protrusion 17), the load that is exerted on the spring 16 can be reduced. Accordingly, the spring 16 is unlikely to fail.

An embodiment of the present invention has been described above, but the present invention is not limited to the above-described embodiment, and various modifications are possible within the scope set forth in the claims. For example, the following modifications can be implemented.

[Modifications]

(1) In the foregoing embodiment, the extender-side engagement part 30 is configured by the above-described slide parts 13 and the protrusion 17, and the tab part-side engagement part 31 is formed by the above-described slide guide parts 27 and the hole 25d, but the present invention is not limited to this, and any configuration is possible as long as the tab parts 25 and the extender 10 can be engaged with each other. For example, a configuration is also possible in which the slide parts 13 are formed so as to extend along the faces of the extender 10 that are parallel to the longitudinal direction, and the slide guide parts 27 are formed so as to extend along the faces of the head part 22 that are parallel to the tube axis direction. Furthermore, the receiving part into which the protrusion 17 of the spring 16 is fitted is not limited to the hole 25d as described above, and may be a recess, a groove, or the like.

(2) In the foregoing embodiment, the extender 10 is configured by two blades 11, but the present invention is not limited to this, and one integrated member may be used as the extender 10. In this case, the operator only needs to apply a twist torque to the extender after reduction so as to twist off the weak parts 26, thereby separating the tab parts 25 from the base part 24.

Figure 12:
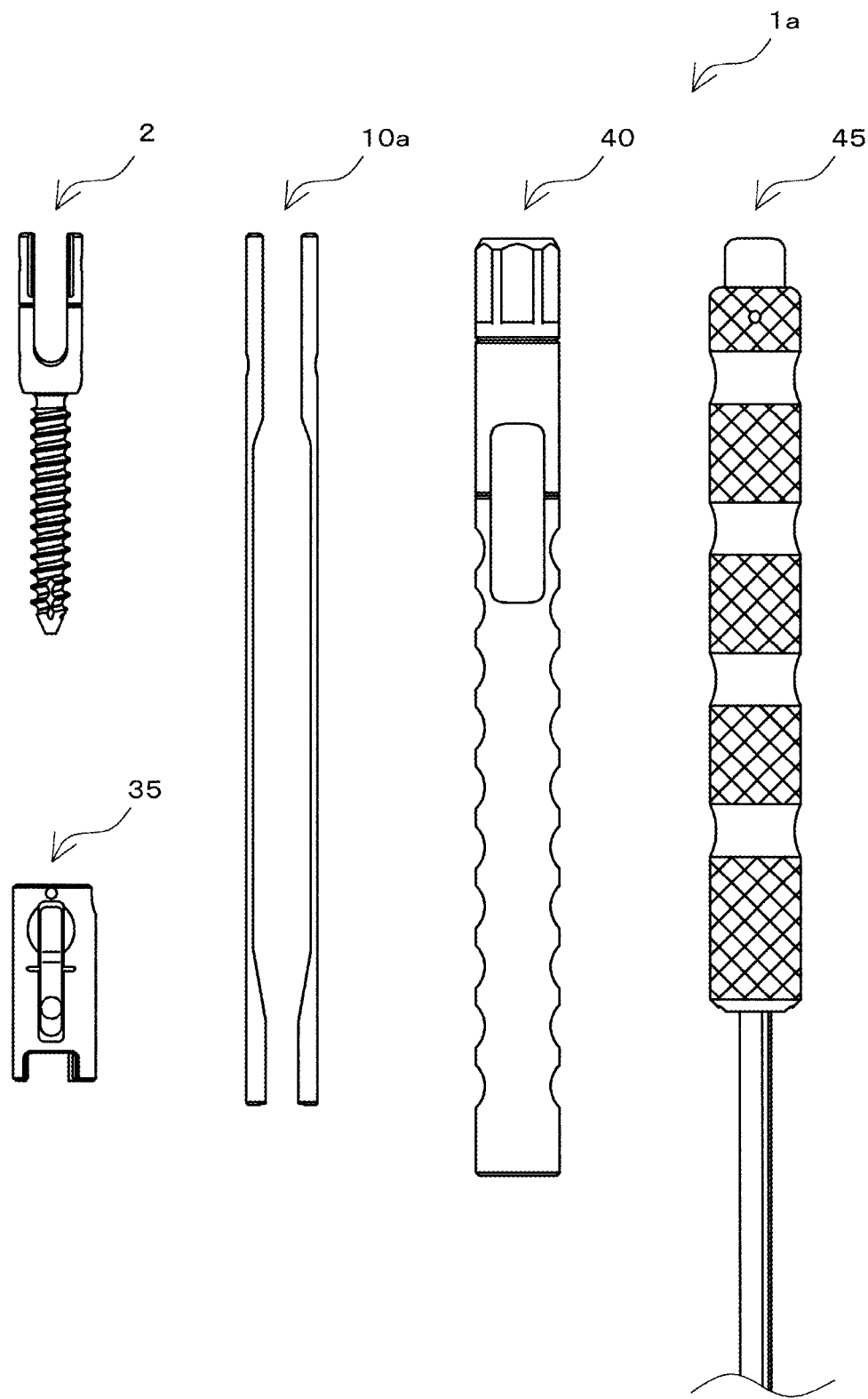
FIG. 12 is a diagram illustrating constituent components included in a spine fixation device according to a modification.

(3) FIG. 12 is a diagram illustrating constituent components included in a spine fixation device 1a according to a modification. The spine fixation device 1a according to the modification includes, as shown in FIG. 12, a reduction screw 2, an extender 10a, a cap 35, an extender guard 40, and a tab remover 45. The reduction screw 2 has the same configuration as that of the foregoing embodiment and thus the description thereof is omitted, and the following will describe configurations of the extender 10a having a configuration different from that of the foregoing embodiment, and the cap 35, the extender guard 40, and the tab remover 45, which are new constituent components. Note that FIG. 12 shows the tab remover 45, a part of which is omitted.

[Extender Configuration]

FIG. 13 illustrate the shape of the extender 10a, with FIG. 13A being a front view and FIG. 13B being a side view. Similarly to the case of the foregoing embodiment, the extender 10a includes two blades 11a, as shown in FIG. 13. The two blades 11a have substantially the same configuration as that of the blades 11 of the foregoing embodiment. However, an elongated member 12b of each blade 11a is configured to have a thickness smaller than that of the elongated member 12 of the foregoing embodiment. Accordingly, if an external force in the thickness direction of the elongated member 12b is applied to one end side in the longitudinal direction of the elongated member 12b in the state in which the other end side in the longitudinal direction of the elongated member 12b is fixed, the elongated member 12 will be elastically deformed relatively significantly in that direction.

Furthermore, the elongated member 12b has a base end part 14, which is a portion on the opposite side of the elongated member 12b to the extender-side engagement part 30 side, and an intermediate part 15, which is a portion between the extender-side engagement part 30 and the base end part 14 of the elongated member 12b, the base end part 14 and the intermediate part 15 being integrally formed.

As shown in FIG. 13A, the base end part 14 has, in its central part, a through-hole 14a that passes through the base end part 14 in the thickness direction thereof. A protrusion 37c that is formed on a blade spring part 37 of the cap 35, which will be described in detail later, fits into the through-hole 14a.

[Cap Configuration]

Figure 14B:
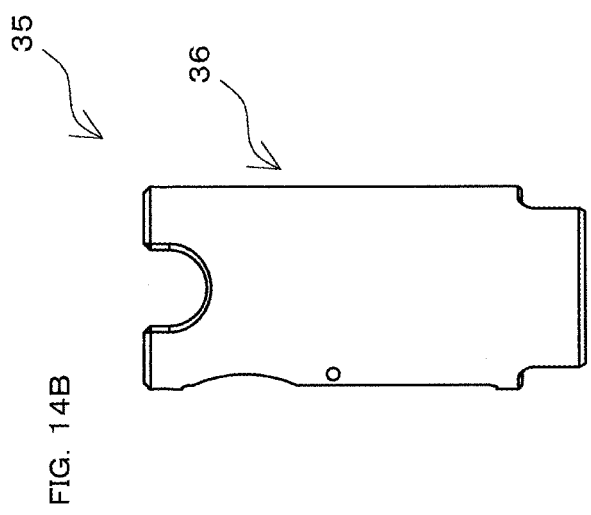
FIG. 14B illustrates the shape of the cap shown in FIG. 12, with FIG. 14B being a side view.
Figure 14A:
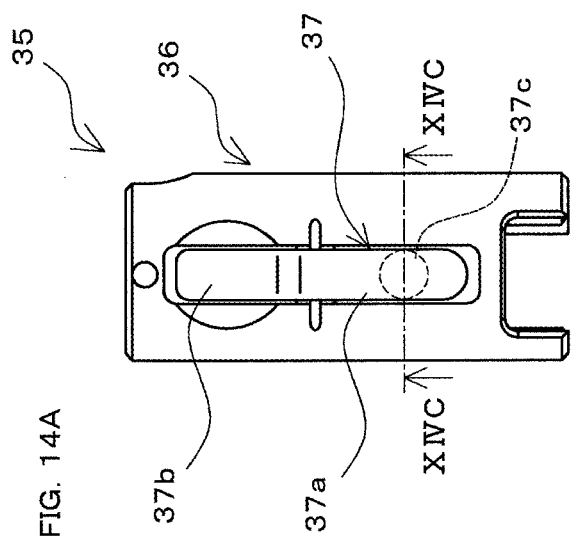
FIG. 14A illustrates the shape of the cap shown in FIG. 12, with FIG. 14A being a front view.
Figure 14C:
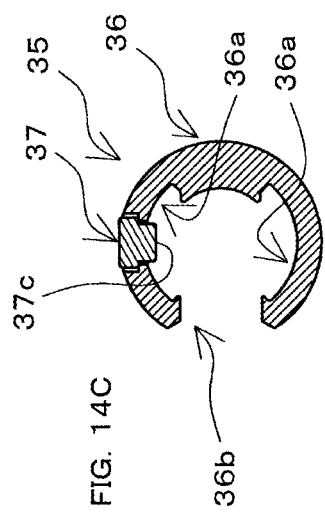
FIG. 14C illustrates the shape of the cap shown in FIG. 12, with FIG. 14C being a cross-sectional view taken along a line XIVC-XIVC of FIG. 14A.

FIG. 14 illustrate the shape of the cap 35, with FIG. 14A being a front view, FIG. 14B being a side view, and FIG. 14C being a cross-sectional view taken along the line XIVC-XIVC of FIG. 14A. The cap 35 is a substantially cylindrical member and is to be mounted on the base end parts 14 of the pair of blades 11a in the state in which they are engaged with the reduction screw 2. As shown in FIG. 14, the cap 35 includes a main body part 36 and the blade spring part 37, which are integrally formed.

The main body part 36 is a substantially cylindrical part of the cap 35. As shown in FIG. 14C, the main body part 36 includes two groove parts 36a and a slit part 36b.

Each groove part 36a is formed on the inner circumference surface of the main body part 36 so as to extend between both ends in the longitudinal direction of the main body part 36. The base end parts 14 of the elongated members 12b are inserted into the groove parts 36a in the direction in which the groove parts 36a extend. The slit part 36b is provided as a portion of the main body part 36 that is cut off from one end to the other in the longitudinal direction of the main body part 36.

The blade spring part 37 is an elongated part extending in the axial direction of the cap 35. The blade spring part 37 is formed so that one end side (front end side) thereof in the longitudinal direction bends with the other end side (base end side) in the longitudinal direction that is fixed to the main body part 36 serving as a fulcrum. The blade spring part 37 has a base end-side portion 37b that is provided at a portion on the opposite side to the side of the main body part 36 on which the extender 10a is inserted, and a front end-side portion 37a that is provided at a portion on the side of the main body part 36 on which the extender 10a is inserted. The blade spring part 37 is provided so as to be exposed on the inner side of the main body part 36. Furthermore, the front end-side portion 37a of the blade spring part 37 has the protrusion 37c that protrudes to the inside of the main body part 36. This protrusion 37c is fitted into the through-hole 14a of the extender 10a in the state in which the pair of blades 11a is inserted into the cap 35.

[Extender Guard Configuration]

Figure 15A:
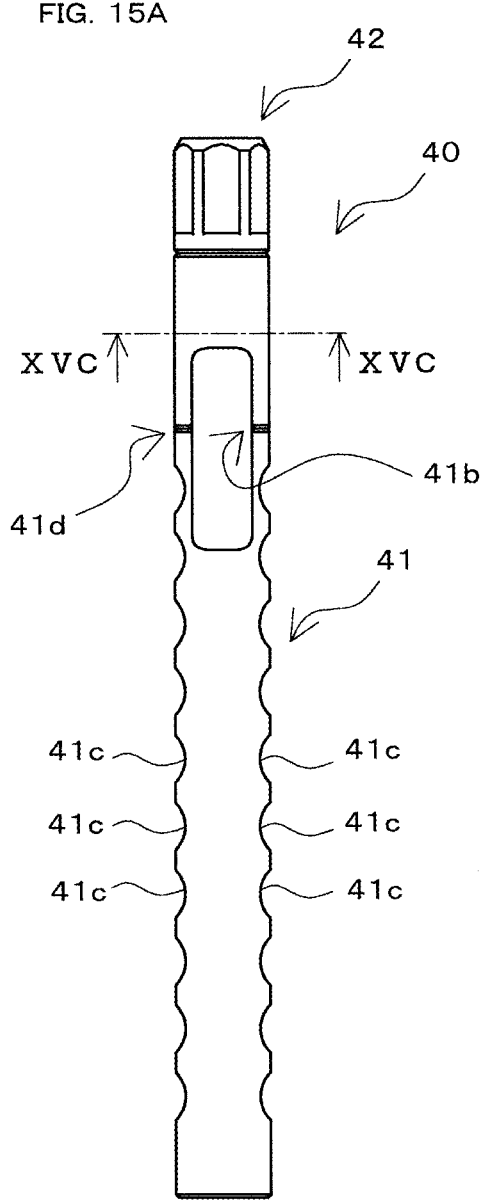
FIG. 15A illustrates the shape of an extender guard shown in FIG. 12, with FIG. 15A being a front view.
Figure 15B:
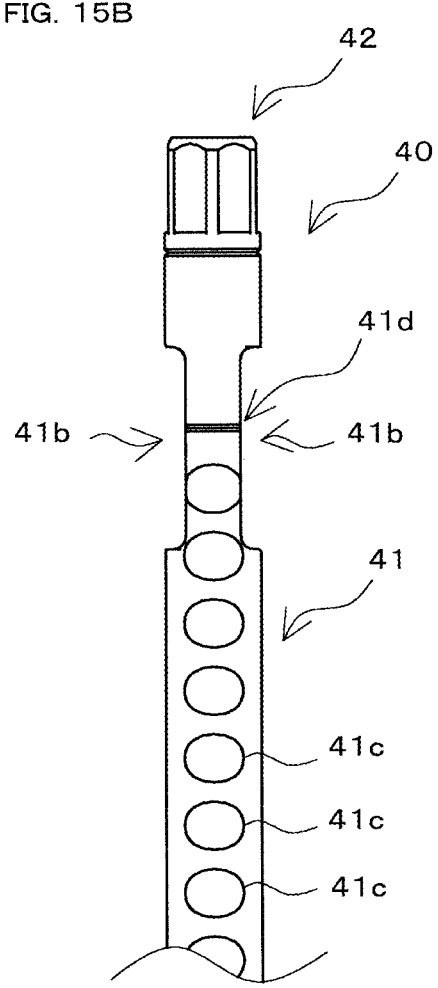
FIG. 15B illustrates the shape of an extender guard shown in FIG. 12, with FIG. 15B being a side view in which a part of the extender guard is omitted.
Figure 15C:
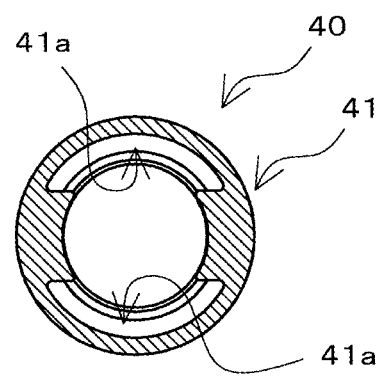
FIG. 15C illustrates the shape of an extender guard shown in FIG. 12, with FIG. 15C being a cross-sectional view taken along a line XVC-XVC of FIG. 15A.

FIG. 15 illustrate the shape of the extender guard 40, with FIG. 15A being a front view, FIG. 15B being a side view in which a part of the extender guard 40 is omitted, and FIG. 15C being a cross-sectional view taken along the line XVC-XVC of FIG. 15A. The extender guard 40 is an elongated and substantially cylindrical member. The extender guard 40 is fixed to the pair of blades 11a in the state in which the pair of blades 11a engaged with the reduction screw 2 are inserted into the through-hole of the extender guard 40. At this time, the extender guard 40 externally covers the base end parts 14 and the intermediate parts 15 of the pair of blades 11a.

As shown in FIG. 15, the extender guard 40 includes a main body part 41 and a hexagonal part 42.

The main body part 41 is an elongated and substantially cylindrical portion of the extender guard 40. The main body part 41 has two groove parts 41a, an opening 41b, and a plurality of recesses 41c.

Each groove part 41a is formed on the inner circumference surface of the main body part 41 so as to extend between both ends in the longitudinal direction of the main body part 41. The base end part 14 and the intermediate part 15 of the elongated member 12b are inserted into this groove part 41a in the direction in which the groove parts 41a extend. The opening 41b is formed in a portion of the main body part 41 on the side on which the hexagonal part 42 is formed. The opening 41b is provided as an elongated through-hole that extends in the longitudinal direction of the main body part 41. Two openings 41b are formed on the main body part 41, and are provided such that the directions of the openings oppose each other. The plurality of recesses 41c are arranged equidistantly in the longitudinal direction of the main body part 41 at positions 180 degrees apart in the circumferential direction of the main body part 41. Furthermore, a marking 41d is formed in the vicinity of the central portions of the openings 41b in the longitudinal direction of the main body part 41. This marking 41d is formed in the shape of, for example, a groove extending in the circumferential direction of the main body part 41.

The hexagonal part 42 is a portion formed in a hexagonal column, and is fixed to a portion on one end side of the main body part 41 so that the central axis of the hexagonal part 42 is coaxial with the central axis of the main body part 41.

[Tab Remover Configuration]

FIG. 16 illustrate the shape of the tab remover 45, with FIG. 16A being a front view, FIG. 16B being a side view, and FIG. 16C being a diagram viewed in the direction of the arrow XVIC of FIG. 16A in which illustration of a grip part and a button is omitted. The tab remover 45 is a tool for cutting off the tab parts 25 of the reduction screw 2 from the base part 24. As shown in FIG. 16, the tab remover 45 has a main body part 46, a grip part 47, and a button 48, and is formed by these constituent components being assembled together.

The main body part 46 is an elongated tubular part. As shown in FIG. 16C, the main body part 46 is formed so as to have a substantially semicircular cross-sectional shape that is hollow inside. Furthermore, the grip part 47 is mounted to one side (upper side of FIGS. 16A and 16B) of the main body part 46. The button 48 is mounted on the upper end side of the grip part 47. The button 48 is provided extending in the vertical direction within the main body part 46, and is configured to move downward by being pressed by the operator, and to move upward to return to the original position (the position shown in FIG. 16) with a spring mechanism (not shown) or the like, by being released by the operator.

[Cap Use Method]

FIG. 17A is a diagram illustrating the cap 35 that is mounted on the extender 10a fixed to the reduction screw 2, together with the reduction screw 2 and the extender 10a. Furthermore, FIG. 17B is a cross-sectional view taken along the line XVIIB-XVIIB of FIG. 17A, illustrating the state in which the extender 10a and the cap 35 are engaged with each other.

With respect to the cap 35, the cap 35 is slid in the longitudinal direction of the extender 10a so that the base end parts 14 of the pair of blades 11a of the extender 10a fixed to the reduction screw 2 are inserted into the pair of groove parts 36a formed in the cap 35. Accordingly, as shown in FIG. 17, the cap 35 externally covers the pair of base end parts 14 so as to prevent the extender 10a fixed to the reduction screw 2 from moving closer to or away from each other.

Furthermore, when, as described above, the cap 35 is slid with respect to the extender 10a so that the extender 10a is inserted into the cap 35, the protrusion 37c, which is formed on the blade spring part 37 of the cap 35, is fitted into the through-hole 14a formed in the base end part 14 of the corresponding blade 11a. Accordingly, the cap 35 can be fixed to the extender 10a in the state of being positioned with respect to the longitudinal direction of the extender 10a. Furthermore, in such a state in which the cap 35 is fixed to the extender 10a, the slit of the slit part 36b of the cap 35 is in communication with the gap between the pair of blades 11a.

As described above, the cap 35 mounted on the extender 10a can prevent the extender 10a from being broken due to an excess load that is exerted on the extender 10a during some sort of procedure in the operation (for example, when the operator inserts the fixing rod into the slits 23 of the reduction screw 2).

[Extender Guard Use Method]

Figure 18A:
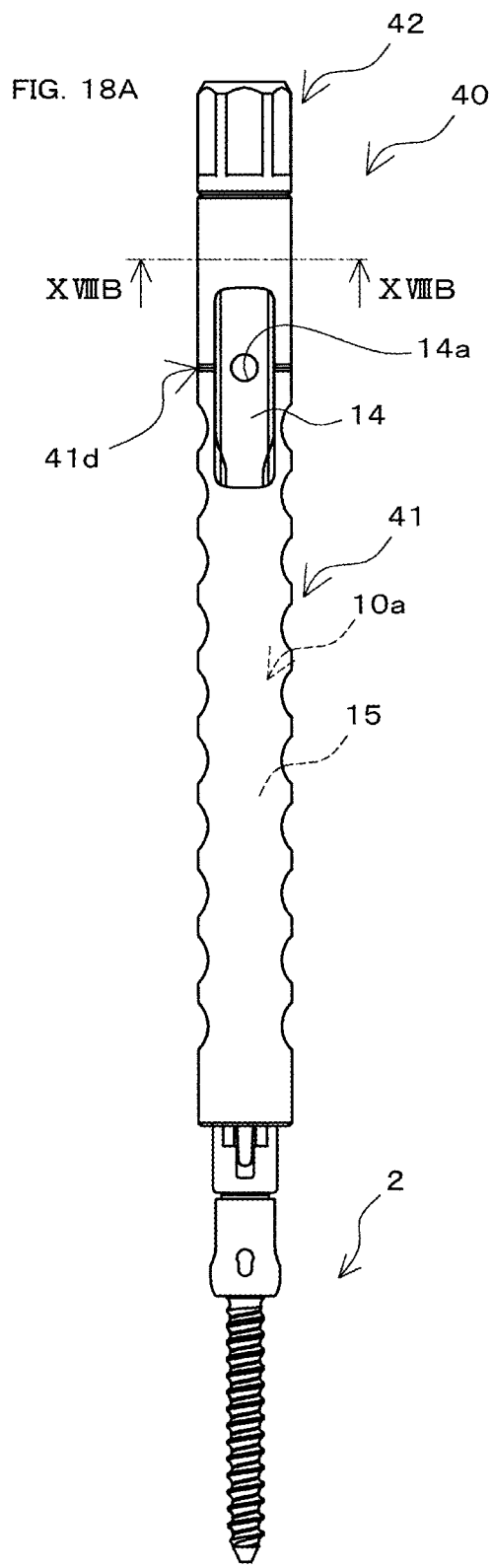
FIG. 18A is a diagram illustrating the extender guard that is mounted on the extender fixed to the reduction screw, together with the reduction screw and the extender.
Figure 18B:
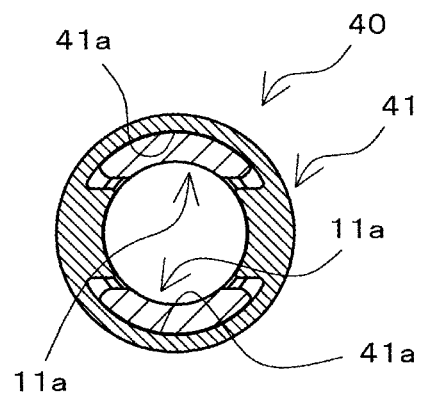
FIG. 18B is a cross-sectional view taken along a line XVIIIB-XVIIIB of FIG. 18A.

FIG. 18A is a diagram illustrating the extender guard 40 that is mounted on the extender 10a fixed to the reduction screw 2, together with the reduction screw 2 and the extender 10a. Furthermore, FIG. 18B is a cross-sectional view taken along the line XVIIIB-XVIIIB of FIG. 18A, illustrating the state in which the extender 10a and the extender guard 40 are engaged with each other.

With respect to the extender guard 40, the extender guard 40 is slid in the longitudinal direction of the extender 10a so that the base end parts 14 and the intermediate parts 15 of the pair of blades 11a of the extender 10a fixed to the reduction screw 2 are inserted into the pair of groove parts 41a formed in the extender guard 40. Accordingly, as shown in FIG. 18, the extender guard 40 externally covers the pair of base end parts 14 and the intermediate parts 15 so as to prevent the extender 10a fixed to the reduction screw 2 from moving closer to or away from each other.

Furthermore, when, as described above, the extender guard 40 is slid with respect to the extender 10a so that the extender 10a is inserted into the extender guard 40, the operator slides the extender guard 40 until the through-holes 14a and the marking 41d are aligned in the longitudinal direction. Accordingly, relative positioning of the extender guard 40 with respect to the extender 10a is possible.

The extender guard 40 that is mounted on the extender 10a as described above can prevent the extender 10a from being broken due to an excess load being exerted on the extender 10a during some sort of procedure in the operation (for example, when the operator performs destruction or construction).

[Tab Remover Use Method]

FIG. 19A is a diagram illustrating the tab remover 45 that is mounted on the extender 10a fixed to the reduction screw 2, together with the reduction screw 2 and the extender 10a. Furthermore, FIG. 19B is a cross-sectional view taken along the line XIXB-XIXB of FIG. 19A, illustrating the state in which the extender 10a and the tab remover 45 are engaged with each other.

With respect to the tab remover 45, the tab remover 45 is slid in the longitudinal direction of the blades 11a so that one of the pair of blades 11a fixed to the reduction screw 2 is covered with the main body part 46 of the tab remover 45. Accordingly, in this state, by the operator gripping the grip part 47 of the tab remover 45 and applying an external force in the direction perpendicular to the longitudinal direction of the blade 11a, the tab part 25 is broken off at the groove part 26a, which is provided as the weak part 26. Accordingly, it is possible to separate the tab part 25 engaged with the blade 11a from the base part 24.

As described above, by the operator pressing the button 48 of the tab remover 45 after the tab part 25 is separated from the base part 24 of the reduction screw 2, the blade 11a inside is pressed by the button 48. Accordingly, it is possible to remove the blade 11a, together with the tab parts 25, from the tab remover 45.

[Effects]

As described above, in the spine fixation device 1a according to the present modification, the blades 11a of the extender 10a are configured by members that are more elastically deformable than the weak part 26 of the reduction screw 2. Accordingly, even if an excessive external force is applied to the extender 10a mounted on the reduction screw 2, the blades 11a will bend. Therefore, even if a large external force is exerted on the extender 10a during the operation for some reason, the tab part 25 can be prevented from being broken.

Furthermore, in the spine fixation device 1a, by mounting the tab remover 45 on the extender 10a and applying an external force to the tab remover 45, it is possible to separate the tab part 25 from the base part 24. It is thus possible to separate the extender 10a, which is more elastically deformable than the weak part 26, together with the tab parts 25, from the base part 24.

Furthermore, in the tab remover 45, it is possible to easily remove the tab part 25 separated from the base part 24, together with the blade 11a, from the tab remover 45 by pressing the button 48.

Furthermore, in the spine fixation device 1a, by using the cap 35, it is possible to prevent the pair of base end parts 14 of the pair of blades 11a from moving closer to or away from each other, without covering a gap (gap into which the fixing rod is inserted) between the pair of intermediate parts 15 formed between the pair of blades 11a. Accordingly, the fixing rod can be guided to the slits 23 in the reduction screw 2 via this gap, in the state in which, for example, the distance between the pair of blades 11a is maintained. Furthermore, in the spine fixation device 1a, since the positions of the pair of blades 11a can be fixed with respect to each other, it is possible to reduce the risk of the blades 11a being bent due to an excessive force being exerted on the blades 11a during the operation.

Furthermore, with respect to the cap 35, the protrusion 37c formed on the blade spring part 37 of the cap 35 fits into the through-hole 14a formed on the base end part 14 of the extender 10a in the state in which the cap 35 is mounted on the extender 10a. Accordingly, the position of the cap 35 with respect to the extender 10a can be fixed in the longitudinal direction of the extender 10a.

Note that with respect to the cap, instead of the blade spring part 37 shown in FIG. 14, a lock part (illustration thereof is omitted) that is shaped similarly to the blade spring part 37 and operates in the manner of a lever may be provided. A base end-side portion (portion that corresponds to the part 37b of FIG. 14) of the lock part is pressed with the central portion in the longitudinal direction thereof serving as a fulcrum, and moves to the inside of the cap, and thereby a protrusion (portion that corresponds to the protrusion 37c of FIG. 14) moves to the outside of the cap. On the other hand, when the pressure is released, the base end-side portion is pressed to return to the outside of the cap by a coil spring (not shown), and thereby the protrusion is returned to the inside of the cap.

When a cap having such a lock part is used, the operator only needs to mount the cap on the extender 10a in the state in which the base end-side portion of the lock part is pressed and then release the pressure. Accordingly, the protrusion is fitted into the through-hole 14a of the extender 10a, and thus, similarly to the foregoing case, the position of the cap can be fixed with respect to the extender 10a in the longitudinal direction of the extender 10a.

Furthermore, in the spine fixation device 1a, since the extender guard 40 can be used to fix the positions of the pair of intermediate parts 15 of the pair of blades 11*a* with respect to each other, it is possible to reduce the risk of the blades 11*a* being bent due to an excessive external force being exerted on the blades 11*a* during the operation.

Furthermore, in the extender guard 40, compression and distraction can be performed in the state in which the front end portions of a compressor and a distractor (illustrations thereof are omitted) are engaged with the recesses 41*c*. Accordingly, it is possible to perform compression and distraction while preventing the front end portions of the compressor and the distractor from sliding with respect to the extender guard 40.

Furthermore, with respect to the extender guard 40, when the extender guard 40 is mounted on the extender 10*a*, it is possible to easily perform positioning of the extender guard 40 in the longitudinal direction thereof with respect to the extender 10*a*, by aligning the position of the marking 41*d* with the positions of the through-holes 14*a* of the extender 10*a*.

The present invention is widely applicable as a spinal implant that is to be implanted in a spine so as to hold a fixing rod for fixing a plurality of vertebrae to each other, and a spine fixation device that includes the spinal implant.

The invention claimed is:

1. A spinal fixation device comprising:
   a screw part having a screw body part configured to be implanted in a spine;
   a head part that is attached to a portion on an opposite side of the screw part to the screw body part and has a slit into which a fixing rod for fixing a plurality of vertebrae is to be inserted, wherein the head part includes:
      a base part that is provided as a portion on the screw part side of the head part and in which the fixing rod inserted into the slit is held; and
      a pair of tab parts that are formed so as to face each other across the slit extend in a first direction, wherein the first direction extends from the base part to an opposite side to the screw part,
      a pair of extenders that each engage a respective tab part from the pair of tab parts, wherein each of the pair of extenders includes a blade that extends in the first direction, and
      weak parts formed between the base part and each of the pair of tab parts, wherein the weak parts are configured to be broken by an external force from the pair of extenders; and
   an extender guard that is substantially cylindrical and elongated in the first direction, wherein the extender guard includes two grooved parts formed on an inner circumference surface of the extender guard that extend in the first direction, wherein the two grooved parts are configured to receive each blade from the pair of extenders.

2. The spinal fixation device according to claim 1, wherein each of the pair of tab parts include:
   a slide guide part that is formed on the tab parts to enable a slide part formed on the extender to slide, and
   a receiving part that is formed on the tab parts and into which a protrusion of a spring of the extender is to fit.

3. The spinal fixation device according to claim 2, wherein the slide guide part is formed, so as to extend in the first direction, in a portion on both sides of the tab parts in a width direction, which is a second direction that is orthogonal to the first direction, so as to enable the slide part of which two are formed on each of the pair extenders to slide.

4. The spinal fixation device according to claim 3, wherein each tab from the pair of tabs further includes a slide guide part and a receiving part that are formed on the tab parts, and
wherein each of the pair of extenders further includes an extender-side engagement part includes a slide part that is able to slide with respect to the slide guide part, and a protrusion that is formed on a spring attached to each of the pair of extenders and is configured to fit into the receiving part formed on the tab parts.

5. The spinal fixation device according to claim 2, wherein the slide part is formed so as to extend in the direction in which the fixing rod is guided in the extender, and
the spring is formed so as to extend in the direction in which the slide part extends, and is provided as a blade spring that has the protrusion formed at one end and is fixed at the other end to each of the pair of extenders.

6. The spinal fixation device according to claim 1, wherein the each blade of the pair of extenders includes guide members are more elastically deformable than the weak parts.

7. The spinal fixation device according to claim 6, wherein each of the pair of extenders further includes: a base end part on an opposite side and separated along in the first direction from an extender-side engagement part; and an intermediate part between the extender-side engagement part and the base end part, and
the spinal fixation device further comprises a cap that is configured to externally cover the base end of each of the pair of extenders so as to restrict each blade of the pair of extenders from moving closer to or away from each other.

8. The spinal fixation device according to claim 1, wherein each of blade of the pair of extenders includes an elongated through-hole that extends in first direction;
   wherein the pair of extenders are configured to position each blade so that each elongated through-hole faces each other.

9. The spinal fixation device according to claim 8, wherein the a pair of extenders each further includes a marking formed in a vicinity of a center of each elongated through-hole, wherein the marking enables a relative positioning of the extender guard with respect to the pair of extenders.

10. The spinal fixation device according to claim 1, further comprising:
    a tab remover that is configured by a member that is less elastically deformable than each blade of each of the pair of extenders and the weak parts, and is configured to separate the pair of tab parts from the base part by the external force being applied to the tab remover mounted on the extender to break the weak parts.

11. The spinal fixation device according to claim 1, wherein the extender guard further includes a plurality of recesses.

* * * * *